United States Patent
Abbas et al.

(10) Patent No.: US 10,961,549 B2
(45) Date of Patent: Mar. 30, 2021

(54) GENES CONFERRING TOLERANCE TO ETHANOL AND HIGH TEMPERATURE FOR YEASTS

(71) Applicant: ARCHER DANIELS MIDLAND COMPANY, Decatur, IL (US)

(72) Inventors: Charles Abbas, Champaign, IL (US); Andriy Sibirny, Lviv (UA); Andriy Voronovsky, Lviv (UA); Olena Ishchuk, Lviv (UA)

(73) Assignee: ARCHER DANIELS MIDLAND COMPANY, Decatur, IL (US)

(*) Notice: Subject to any disclaimer, the term of this patent is extended or adjusted under 35 U.S.C. 154(b) by 0 days.

(21) Appl. No.: 15/215,748

(22) Filed: Jul. 21, 2016

(65) Prior Publication Data

US 2017/0218402 A1    Aug. 3, 2017

Related U.S. Application Data

(62) Division of application No. 14/358,876, filed as application No. PCT/US2013/021100 on Jan. 11, 2013, now Pat. No. 9,428,559.

(60) Provisional application No. 61/585,873, filed on Jan. 12, 2012.

(51) Int. Cl.
*C07K 14/39* (2006.01)
*C07K 14/395* (2006.01)
*C12P 7/06* (2006.01)
*C12N 15/81* (2006.01)
*C12Q 1/6811* (2018.01)

(52) U.S. Cl.
CPC .............. *C12P 7/06* (2013.01); *C07K 14/39* (2013.01); *C07K 14/395* (2013.01); *C12N 15/81* (2013.01); *C12N 15/815* (2013.01); *C12Q 1/6811* (2013.01); *Y02E 50/10* (2013.01)

(58) Field of Classification Search
None
See application file for complete search history.

(56) References Cited

U.S. PATENT DOCUMENTS

| | | | | |
|---|---|---|---|---|
| 9,200,291 B2* | 12/2015 | Zieler | ............... | C12N 15/1027 |
| 9,388,399 B2* | 7/2016 | Abbas | ............... | C12N 9/242 |
| 9,428,559 B2* | 8/2016 | Abbas | ............... | C12P 7/06 |
| 9,441,255 B2* | 9/2016 | Tian | ............... | C07K 14/37 |
| 9,598,689 B2* | 3/2017 | Argyros | ............... | C07K 14/38 |
| 10,577,580 B2* | 3/2020 | Abbas | ............... | C12N 15/01 |
| 2004/0167066 A1* | 8/2004 | Marzioch | ............... | C07K 14/39 435/6.16 |
| 2012/0322078 A1* | 12/2012 | McBride | ............... | C12P 7/04 435/6.18 |
| 2014/0170708 A1* | 6/2014 | Zieler | ............... | C12N 15/1027 435/91.2 |
| 2014/0220641 A1* | 8/2014 | Tian | ............... | C07K 14/37 435/99 |
| 2014/0356879 A1* | 12/2014 | Abbas | ............... | C12P 7/06 435/6.15 |
| 2015/0329853 A1* | 11/2015 | Zieler | ............... | C12N 15/1027 506/26 |
| 2017/0010117 A1* | 1/2017 | Oh | ............... | G01C 21/3492 |
| 2017/0191088 A1* | 7/2017 | Argyros | ............... | C12P 7/10 |
| 2017/0218402 A1* | 8/2017 | Abbas | ............... | C12N 15/907 |

FOREIGN PATENT DOCUMENTS

| | | | | |
|---|---|---|---|---|
| EP | 1258493 A1 * | 11/2002 | ............... | C07K 14/39 |
| EP | 1338608 A2 * | 8/2003 | ............... | C07K 14/39 |
| WO | WO-2011022651 A1 * | 2/2011 | ............... | C12P 7/04 |
| WO | WO-2013106617 A2 * | 7/2013 | ............... | C12P 7/06 |
| WO | WO-2014100400 A1 * | 6/2014 | ............... | C12N 15/1027 |

OTHER PUBLICATIONS

Ishchuk et al, Biotechnology and Bioengineering. 2009, 104:911-919. published online Jul. 2, 2009 (Year: 2009).*
Hu et al, Genetic Dissection of Ethanol Tolerance in the Budding Yeast *Saccharomyces cerevisiae*. Genetics, Mar. 2007. 175: 1479-1487 (Year: 2007).*
Gray et al, Bioethanol. Current Opinion in Chemical Biology, 2006, 10:141-146. available online Mar. 7, 2006 (Year: 2006).*
Alper et al, Science, 2006, 314:15651568. Dec. 8, 2006 (Year: 2006).*
Prasad et al, Resources, Conservation and Recycling, 2007, 50:1-39. available online Jul. 3, 2006 (Year: 2006).*
Brachmann, C.B., A. Davies, G.J. Cost, E. Caputo , J. Li , P. Hieter , and J.D. Boeke. 1998. Designer strains derived from *Saccharomyces cerevisiae* S288C: useful set of strains and plasmids for PCR-mediated gene disruption and other applications.Yeast 14: 115-132.

(Continued)

*Primary Examiner* — Nita M. Minnifield
(74) *Attorney, Agent, or Firm* — Mark W. Roberts

(57) ABSTRACT

Methods of identifying genes conferring ethanol tolerance in yeasts, genes that confer ethanol tolerance, and mutant strains used to identify such genes are described. A gene herein designated HpETT1 was isolated from the yeast *Hansenula polymorpha*. Expression of HpETT1 in an ethanol sensitive mutant *H. polymorpha* strain designated 7E complimented ethanol sensitivity of the mutant. When multiple copies of the HpETT1 were integrated into the genome and overexpressed, the transformed strain demonstrated approximately 10-fold greater resistance to ethanol and resistance to the protein misfolding agent AZC. Expression of HpETT1 also increased ethanol tolerance in *Saccharomyces cerevisiae*. HpEtt1 has 39% sequence identity to a previously identified protein from *S. cerevisiae* denoted MPE1, however, the MPE1 gene does not confer ethanol resistance to the 7E mutant. Another gene from the yeast *Pichia stipites* was identified that encodes an orthologue protein having 37% identity to HpETT1 herein designated PsETT1 and also confers ethanol resistance to the 7E mutant.

6 Claims, 14 Drawing Sheets

Specification includes a Sequence Listing.

(56) References Cited

OTHER PUBLICATIONS

Brodsky, A. S. and Silver, P. A. (2000). Pre-mRNA processing factors are required for nuclear xport. RNA 6: 1737-1749.

Faber, K.N., P. Haima, W. Harder, M. Veenhuis, and G. Ab. 1994. Highly-efficient electrotransformation of the yeast Hansenula polymorpha. Curr Genet 25(4): 305-310.

Gellissen, G. 2000. Heterologous protein production in methylotrophic yeasts. Appl. Microbiol. Biotechnol. 54: 741-750.

Gleeson, M.A.G. and P.E. Sudbery. 1988. Genetic analysis in the methylotrophic yeast Hansenula polymorpha. Yeast 4: 293-303.

Guerra, E., P.P. Chye, E. Berardi and P.W. Piper. 2005. Hypoxia abolishes transience of the heat-shock response in the methylotrophic yeast Hansenula polymorpha. Microbiology 151: 805-811.

Ishchuk, O.P., A.Y. Voronovsky, O.V. Stasyk, G.Z. Gayda, M.V. Gonchar, C.A. Abbas, and A.A. Sibimy. 2008. Overexpression of pyruvate decarboxylase in the yeast Hansenula polymorpha results in increased ethanol yield in high-temperature fermentation of xylose. FEMS Yeast Res 7: 1167-1174.

Jensen, T. H., K. Patricio, T. McCarthy and M. Rosbash. 2001. A block to mRNA nuclear export in *S. cerevisiae* leads to hyperadenylation of transcripts that accumulate at the site of transcription. Mol Cell 7: 887-898.

Krebber, H., T. Taura, M.S. Lee and P.A. Silver. 1999. Uncoupling of hnRNP Npl3p from mRNAs during the stress-induced block in mRNA export. Genes Dev 13: 1994-2004.

Lahtchev, K.L., V.D. Semenova, I.I. Tolstorukov, I. van der Klei, and M. Veenhuis. 2001. Isolation and properties of genetically defined strains of the methylotrophic yeast Hansenula polymorpha CBS4732. Arch. Microbiol. 177: 150-158.

Lane, J.M., P. Dehm, and D.J. Prockop. 1971. Effect of the proline analogue azetidine-2-carboxylic acid on collagen synthesis in vivo. I. Arrest of collagen accumulation in growing chick embryos. Biochim Biophys Acta 236(3): 517-527.

Ryabova, O.B., O.M. Chmil, and A.A. Sibimy. 2003. Xylose and cellobiose fermentation to ethanol by the thermotelerant methylotrophic yeast Hansenula polymorpha. FEMS Yeast Res. 4(2): 157-164.

Saavedra, C., K. S. Tung, D.C. Amberg, A.K. Hopper, and C.N. Cole. 1996. Regulation of mRNA export in response to stress in *Saccharomyces cerevisiae*. Genes Dev 10: 1608-1620.

Siverio, J. M. 2002. Biochemistry and genetics of nitrate assimilation. In . Gellissen (ed.), Hansenula polymorpha—Biology and Applications. Wiley-VCH, Weinheim.

Sohn, J.H., E.S. Choi, H.A. Kang, J.S. Rhee, M.O. Agaphonov, M.D. Ter-Avanesyan, and S.K. Rhee. 1999. A dominant selection system designed for copynumber—controlled gene integration in Hansenula polymorpha DL-1. Appl. Microbiol. Biotechnol. 51: 800-807.

Suckow, M., and G. Gellissen. 2002. The expression platform based on H. polymorpha strain RB11 and its derivatives—history,status and perspectives. In G. Gellissen (ed.), Hansenula polymorpha—Biology and Applications. Wiley-VCH, Weinheim.

Tani, T., R.J. Derby, Y. Hiraoka, and D.L. Spector. 1995. Nuclear accumulation of poly (A)+RNA in heat-shocked yeast cells: implication of nucleolar involvement in mRNA transport. Mol. Biol. Cell 6: 1515-1534.

Trotter, E.W., C.M. Kao, L. Berenfeld, D. Botstein, G.A. Petsko, and J.V. Gray. 2002. Misfolded proteins are competent to mediate a subset of the responses to heat shock in *Saccharomyces cerevisiae*. J Biol Chem 277(47): 44817-44825.

Ubiyvovk, V.M., O.V. Blazhenko, D. Gigot, M. Penninckx, and A.A. Sibimy. 2006. Role of gamma-glutamyltranspeptidase in detoxification of xenobiotics in the yeasts Hansenula polymorpha and *Saccharomyces cerevisiae*. Cell Biol Int 30: 665-671.

Vo, L T., M. Minet, J. M. Schmitter, F. Lacroute, and F. Wyers. 2001. Mpe1, a zinc knuckle protein, is an essential component of yeast cleavage and polyadenylation factor required for the cleavage and polyadenylation of mRNA. Mol. Cell Biol. 21(24): 8346-8356.

Voronovsky, A., C.A. Abbas, L.R. Fayura, B.V. Kshanovska, K.V. Dmytruk, K.A. Sybirna and A.A. Sibirny. 2002. Development of a transformation system for the flavinogenic yeast Candida famata. FEMS Yeast Res. 2: 381-388.

Yang, V.W., J.A. Marks, B. Davis, and T. Jeffries. 1994. High-efficiency transformation of Pichia stipitis based on its URA3 gene and a homologous autonomous replication sequence, ARS2. Appl. Environ. Microbiol. 60: 4245-4254.

Zagari, A., G. Némethy, and H.A. Scheraga. 1990. The effect of the L-azetidine-2-carboxylic acid residue on protein conformation. I. Conformations of the residue and of dipeptides. Biopolymers 30(9-10): 951-959.

\* cited by examiner

Figure 4
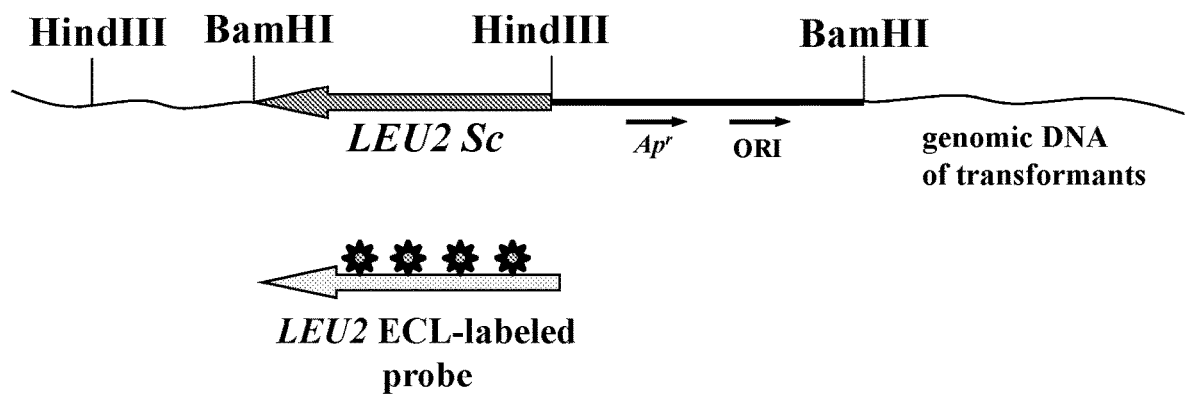
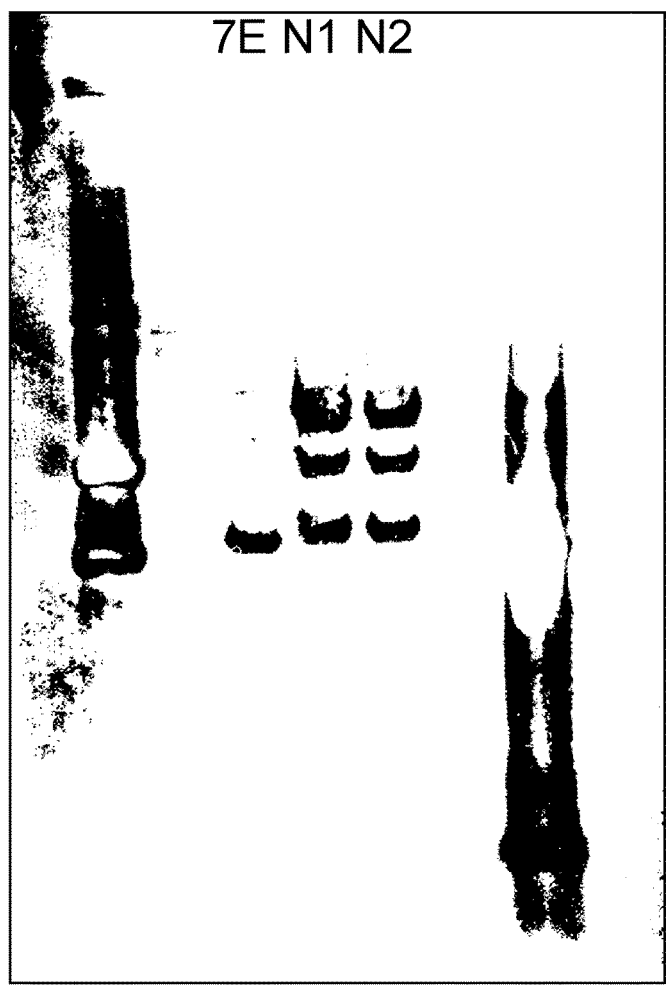
Figure 5

Figure 6

SEQUENCE LISTING

<160> NUMBER OF SEQ ID NOS: 14

<210> SEQ ID NO 1
<211> LENGTH: 1122
<212> TYPE: DNA
<213> ORGANISM: Hansenula polymorpha

<400> SEQUENCE: 1

```
atggctgtca tatactataa gttcagatcg caacgcgatg acttgatttc gaccatcaag    60
tttgatggta ctgggcttac ggtattcgaa ctcaaacgag aaattattta tgccaataag   120
ctgattaatt ccacggacac agatatttta ttatatcatg ttgaagatcc agataaggag   180
tacgacgatg ataatgaagt catacaacga gcatcaacag tgctagtaag aagaacttca   240
ggtggcaaga aaggaagagg aaacgttttg cgatatatgc caggaaagcc aaggattgca   300
aaatttcaag ctccgattcc agtctcaacg acagattcag caccggtcat acctactaat   360
gaagaggaga gaattcgtca gatgttcaat cagcaggacg accagtggaa tcaacaacag   420
gctctcatgg ccactgcaca aagagtggaa agtaatagac aaaatttgaa acttgatgaa   480
aacattcctg aatattacat ttgctataaa tgcggcgaga aagggaaaca tcatattaga   540
aactgtccaa agaataatga tcccaattgg gatggcatca ggatcaaaaa aacgactgga   600
ataccaaaat cgtatttacg cactgttgat aatccgactg acatcgtcaa cgaacctaat   660
cagaacttca tggtgaatga agagggaaaa tacgtggtgg cagttgctga taaaaaagcg   720
tggcaaagat atcagaccat tcagcaatct aagcaagagg aagacgattt cccgattgaa   780
gatcctgaac taagggatcc tcattcaggt aagctttgga aaactcctgt gagaactaaa   840
tgttgcaaac aactgtattc aagaccttac attgaagatc tacttttgga gtcagatttc   900
aagtgtccga attgtggtca agaggacatt tatcttgatt ctcttgaagt cgacgaggca   960
ttacagcgaa aggtagattt gtttgtggaa caacataaga gaaaaaatga aagggaagaa  1020
gagccgaaca agcggcaaca cttagctaca atggtaccta ctatgatgcc atttatgccg  1080
tttccagccc cattgcctct accgaccaat aatcaaaagt ga                    1122
```

```
<210> SEQ ID NO 2
<211> LENGTH: 373
<212> TYPE: PRT
<213> ORGANISM: Hansenula polymorpha

<400> SEQUENCE: 2

Met Ala Val Ile Tyr Tyr Lys Phe Arg Ser Gln Arg Asp Asp Leu Ile
1               5                   10                  15

Ser Thr Ile Lys Phe Asp Gly Thr Gly Leu Thr Val Phe Glu Leu Lys
            20                  25                  30

Arg Glu Ile Ile Tyr Ala Asn Lys Leu Ile Asn Ser Thr Asp Thr Asp
        35                  40                  45

Ile Leu Leu Tyr His Val Glu Asp Pro Asp Lys Glu Tyr Asp Asp Asp
    50                  55                  60

Asn Glu Val Ile Gln Arg Ala Ser Thr Val Leu Val Arg Arg Thr Ser
65                  70                  75                  80

Gly Gly Lys Lys Gly Arg Gly Asn Val Leu Arg Tyr Met Ala Gly Lys
                85                  90                  95

Pro Arg Ile Ala Lys Phe Gln Ala Pro Ile Pro Val Ser Thr Thr Asp
            100                 105                 110

Ser Ala Pro Val Ile Pro Thr Asn Glu Glu Arg Ile Arg Gln Met
        115                 120                 125

Phe Asn Gln Gln Asp Asp Gln Trp Asn Gln Gln Ala Leu Met Ala
    130                 135                 140

Thr Ala Gln Arg Val Glu Ser Asn Arg Gln Asn Leu Lys Leu Asp Glu
145                 150                 155                 160

Asn Ile Pro Glu Tyr Tyr Ile Cys Tyr Lys Cys Gly Glu Lys Gly Lys
                165                 170                 175

His His Ile Arg Asn Cys Pro Lys Asn Asn Asp Pro Asn Trp Asp Gly
            180                 185                 190

Ile Arg Ile Lys Lys Thr Thr Gly Ile Pro Lys Ser Tyr Leu Arg Thr
        195                 200                 205

Val Asp Asn Pro Thr Asp Ile Val Asn Glu Pro Asn Gln Asn Phe Met
    210                 215                 220

Val Asn Glu Glu Gly Lys Tyr Val Val Ala Val Ala Asp Lys Lys Ala
225                 230                 235                 240

Trp Gln Arg Tyr Gln Thr Ile Gln Gln Ser Lys Gln Glu Glu Asp Asp
                245                 250                 255

Phe Pro Ile Glu Asp Pro Glu Leu Arg Asp Pro His Ser Gly Lys Leu
            260                 265                 270

Trp Lys Thr Pro Val Arg Thr Lys Cys Cys Lys Gln Leu Tyr Ser Arg
        275                 280                 285

Pro Tyr Ile Glu Asp Leu Leu Glu Ser Asp Phe Lys Cys Pro Asn
    290                 295                 300

Cys Gly Gln Glu Asp Ile Tyr Leu Asp Ser Leu Glu Val Asp Glu Ala
305                 310                 315                 320

Leu Gln Arg Lys Val Asp Leu Phe Val Glu Gln His Lys Arg Lys Asn
                325                 330                 335

Glu Arg Glu Glu Glu Pro Asn Lys Arg Gln His Leu Ala Thr Met Val
            340                 345                 350

Pro Thr Met Met Pro Phe Met Pro Phe Pro Ala Pro Leu Pro Leu Pro
        355                 360                 365

Thr Asn Asn Gln Lys
    370
```

<210> SEQ ID NO 3
<211> LENGTH: 1425
<212> TYPE: DNA
<213> ORGANISM: Pichia stipitis

<400> SEQUENCE: 3

```
atgtcgtcag tcgtctacta taagttttt caccagaaga accggtcagt gatccacttt      60
gacggtacag ctatatccgt cttcgatctc aagcgagaga ttatccagca gaaccagcta     120
ggactgggtc ttgacttcaa tttacgttta tatcattcag aactgcccga cacagagtat     180
gagttagacc aggatgtcat accgaggtcg tcctacgtct tggcgaaaag gtctcctgct     240
atatttagga acagatttag taccaatgct tccagatatg ttacaggaaa gccacggatc     300
aacagaaaag ccatcaacac cgctggaata acgactggtg tcacaggacc aactctcggc     360
caaagaccag tggacgaaaa catttcggaa gaagatcgaa tcaagttgat gtttgagaac     420
caggagaatg cctgggccca gactcaggac gagttggcca ctcacaaaat gatacactac     480
aagcctggag ccgctggagc taaggaagac ttaccgccac caggttatat tgctataga      540
tgtgggaaga aagaccactg gatcaagaac tgtcctacga caacgaccc caatttcgag      600
ggaaagaagg tcttgcgtac gaccggtatt ccaaagtcgt atttgaagac aatttctaag     660
gaggagtttg acaagaaaat ggagaccgat gcttttgaaa ctaacgaaaa tggagacatt     720
attgatagcg aaggcaatgc cattttagtg acagaagacg gagactatgc catagccatg     780
gctgacagca gacctggct cacataccag gaaaagcaac agaatgctgc cttgaaggca     840
cagcaggact ttgaaaagaa gatagtggct tgcatagaaa acgataatcg agcagagttc     900
ttggatcctc tagcttccac taagaagttg ctcaagtcgc ccatagtgat gacaccatgt     960
tgcaccgaaa agtccaaatt gaacaaaatg accaatttca gctataacaa aagcgcattg    1020
gagcaggtat taattgagaa tgacttccat tgccccaact gtaacaccga agatatcttc    1080
atcgattcct tgattcccaa tgaagagtta gagtcgcagt tgaaacagta catcgaagag    1140
aaacacacag aactaggcat agagattcca ggctcagaaa gcacattaaa agatcagcg    1200
gacgatgcag atgaaatagg cccagatgct aaaagacaac gtccagaaat ggccacccca    1260
tttggtcaaa tgatgcctgg aatgcccatg ccacctccag gagtcatgcc acctccagga    1320
gtcatgcctg ctcctttgc tatccctcca ggtatgccca tccctcctcc cggtatgcca    1380
atgttcatgc ctttcagcaa tgtcaataac agaagaagaa attag                    1425
```

<210> SEQ ID NO 4
<211> LENGTH: 498
<212> TYPE: PRT
<213> ORGANISM: Pichia stipitis

<400> SEQUENCE: 4

```
Met Ser Ser Val Val Tyr Tyr Lys Phe Leu His Gln Lys Asn Lys Ser
1               5                   10                  15

Val Ile His Phe Asp Gly Thr Ser Ile Ser Val Phe Asp Leu Lys Lys
            20                  25                  30

Glu Ile Ile Ile Gln Asn Gln Leu Gly Ser Gly Gln Asp Phe Asn Leu
        35                  40                  45

Arg Leu Tyr His Ser Glu Gln Pro Asp Gln Glu Tyr Glu Leu Asp Gln
    50                  55                  60

Asp Val Ile Pro Arg Ser Ser Tyr Val Leu Ala Lys Arg Ser Pro Ala
65                  70                  75                  80
```

```
Phe Val Lys Ser Gly Lys Tyr Asn Asn Ala Ser Arg Tyr Ile Thr Gly
                85                  90                  95

Lys Pro Arg Ile Asn Arg Lys Ala Ile Thr Ser Thr Val Gly His Asn
            100                 105                 110

Ser Asn Ser Asn Pro Leu Val Ser Ala Gln Leu Gln Gln Gln Gln Gln
        115                 120                 125

Gln Gln Leu Asp Glu Asn Ala Thr Glu Glu Asp Arg Ile Lys Leu Met
    130                 135                 140

Phe Gln Asn Gln Ser Asn Ala Trp Glu Gln Thr Gln Glu Asp Leu Ala
145                 150                 155                 160

His His Lys Met Val Phe Asn Lys Pro Thr Ala Ser Ser Thr Ala Asn
                165                 170                 175

Lys Gln Asp Asp His Pro Pro Gly Tyr Ile Cys Tyr Arg Cys Gly
            180                 185                 190

Lys Lys Asp His Trp Ile Lys Asn Cys Pro Thr Asn Asn Asp Pro Asn
        195                 200                 205

Phe Glu Gly Lys Lys Ile Met Arg Thr Thr Gly Ile Pro Lys Ser Tyr
210                 215                 220

Leu Lys Thr Ile Ser Arg Glu Glu Val Glu Ser Lys Ala Asn Thr Leu
225                 230                 235                 240

Thr Thr Asn Asp Asn Gly Asp Val Val Asp Ser Glu Gly Asn Val Ile
            245                 250                 255

Leu Ile Thr Asp Asp Gly Asp Tyr Ala Ile Ala Met Ala Asp Ser Lys
            260                 265                 270

Thr Trp Gln Asn Tyr Gln Glu Lys Leu Gln Asn Ala Ala Leu Lys Ser
        275                 280                 285

Lys Arg Glu Tyr Glu Ser Lys Leu Val Ala Gly Ile Glu Lys Asp Asn
    290                 295                 300

Lys Trp Glu Phe Leu Asp Pro Leu Ala Asn Thr Lys Ala Val Leu Thr
305                 310                 315                 320

Ser Pro Ile Val Met Thr Pro Cys Cys Thr Asp Ser Ser Lys Leu Gln
                325                 330                 335

Asn Leu Lys Asn Phe Asn Tyr Asn Gln Pro Glu Leu Glu Arg Val Leu
            340                 345                 350

Ile Asp Asn Asp Phe His Cys Pro Asn Cys Gly Lys Ala Asp Val Phe
        355                 360                 365

Leu Asp Ser Val Ile Pro Asn Lys Asp Leu Glu Glu Lys Leu Lys Glu
    370                 375                 380

Tyr Val Ser Ser Lys Glu Lys Glu Leu Asn Ile Lys Asp Pro Ser Lys
385                 390                 395                 400

Arg Thr Ala Ala Glu Met Thr Ala Asp Asp Asn Asn Asp Pro His His
                405                 410                 415

Ser Gly Glu Pro Asp Ala Lys Lys Gln Lys Ile Val Pro Asn Thr Val
            420                 425                 430

Gln Pro Gly Met Phe Pro Val Gly Val Met Pro Pro Pro Pro Pro
        435                 440                 445

Met Pro Phe Ala Leu Pro Pro Gly Leu Gln Ile Pro Pro Gly Phe
    450                 455                 460

Gly Met Val Pro Pro Asn Phe Met Pro Thr Gln Gly Gln Gln
465                 470                 475                 480

Phe Asn Asn Asn Asn Asn Asn Asn Ser Asn Gln Phe Asn Gln
            485                 490                 495
```

Pro Lys

<210> SEQ ID NO 5
<211> LENGTH: 1326
<212> TYPE: DNA
<213> ORGANISM: Saccharomyces cerevisiae

<400> SEQUENCE: 5

```
atgagtagca cgatattta ccgctttaag tctcaacgaa acacatcaag aattttattt      60
gatggtaccg gcctgacagt atttgatttg aaaagggaaa ttattcaaga gaacaaacta     120
ggtgacggca cagatttcca attaaaaatt tacaacccag atacagaaga ggaatacgac     180
gatgatgcct ttgttatacc tagatctact agtgtcatag taaaaagatc tccagcaatt     240
aaatcattct ccgtacacag tcgacttaaa gggaatgtgg gagcagcagc tcttgggaac     300
gcaacaaggt atgttactgg taggccaaga gtgttgcaaa agagacaaca cactgctaca     360
accactgcta atgttagtgg tacaacggaa gaagaaagaa ttgctagtat gtttgccaca     420
caagaaaatc aatgggaaca aacgcaagaa gaaatgtctg cagccacacc tgtttttttc     480
aagtcacaga cgaataagaa ttctgcacaa gaaacgaag gcccaccgcc accaggttat     540
atgtgctatc gttgtggggg tagagaccac tggattaaaa attgtccaac taacagcgat     600
ccaaatttg aaggaaaag aatcagaaga accacaggta ttccaaagaa gttttaaaa      660
tccattgaaa tagatcccga gacaatgaca ccggaagaga tggctcagcg aaagattatg     720
attacggacg aaggcaagtt cgtggtacaa gttgaagaca acaatcatg ggaagactac     780
caaaggaaaa gagagaaccg tcaaattgat ggtgatgaaa ccatttggag aaaaggccat     840
ttcaaagatc ttcctgacga tttaaaatgt cccttgacag gtggtctttt gaggcagccg     900
gtaaagacaa gcaagtgctg taacatagat ttctcaaaag aggcgctgga aaatgcactg     960
gtagagagcg actttgtatg ccccaattgc gaaacccgcg atatccttct cgattcttta    1020
gtacccgacc aggacaagga aaaggaggtc gaaacgtttt tgaagaaaca agaggaacta    1080
cacggaagct ctaaagatgg caaccagcca gaaactaaga aaatgaagtt gatggatcca    1140
actggcaccg ctggcttgaa caacaatacc agccttccaa cttctgtaaa taacggcggt    1200
acgccagtgc caccagtacc gttacctttc ggtatacctc ctttcccat gtttccaatg    1260
cccttcatgc ctccaacggc tactatcaca atcctcatc aagctgacgc aagccctaag    1320
aaatga                                                                1326
```

<210> SEQ ID NO 6
<211> LENGTH: 441
<212> TYPE: PRT
<213> ORGANISM: Saccharomyces cerevisiae

<400> SEQUENCE: 6

```
Met Ser Ser Thr Ile Phe Tyr Arg Phe Lys Ser Gln Arg Asn Thr Ser
1               5                   10                  15

Arg Ile Leu Phe Asp Gly Thr Gly Leu Thr Val Phe Asp Leu Lys Arg
            20                  25                  30

Glu Ile Ile Gln Glu Asn Lys Leu Gly Asp Gly Thr Asp Phe Gln Leu
        35                  40                  45

Lys Ile Tyr Asn Pro Asp Thr Glu Glu Tyr Asp Asp Asp Ala Phe
    50                  55                  60

Val Ile Pro Arg Ser Thr Ser Val Ile Val Lys Arg Ser Pro Ala Ile
65                  70                  75                  80
```

```
Lys Ser Phe Ser Val His Ser Arg Leu Lys Gly Asn Val Gly Ala Ala
                85                  90                  95

Ala Leu Gly Asn Ala Thr Arg Tyr Val Thr Gly Arg Pro Arg Val Leu
            100                 105                 110

Gln Lys Arg Gln His Thr Ala Thr Thr Ala Asn Val Ser Gly Thr
        115                 120                 125

Thr Glu Glu Glu Arg Ile Ala Ser Met Phe Ala Thr Gln Glu Asn Gln
    130                 135                 140

Trp Glu Gln Thr Gln Glu Met Ser Ala Ala Thr Pro Val Phe Phe
145                 150                 155                 160

Lys Ser Gln Thr Asn Lys Asn Ser Ala Gln Glu Asn Glu Gly Pro Pro
                165                 170                 175

Pro Pro Gly Tyr Met Cys Tyr Arg Cys Gly Gly Arg Asp His Trp Ile
            180                 185                 190

Lys Asn Cys Pro Thr Asn Ser Asp Pro Asn Phe Glu Gly Lys Arg Ile
        195                 200                 205

Arg Arg Thr Thr Gly Ile Pro Lys Lys Phe Leu Lys Ser Ile Glu Ile
    210                 215                 220

Asp Pro Glu Thr Met Thr Pro Glu Glu Met Ala Gln Arg Lys Ile Met
225                 230                 235                 240

Ile Thr Asp Glu Gly Lys Phe Val Val Gln Val Glu Asp Lys Gln Ser
                245                 250                 255

Trp Glu Asp Tyr Gln Arg Lys Arg Glu Asn Arg Gln Ile Asp Gly Asp
            260                 265                 270

Glu Thr Ile Trp Arg Lys Gly His Phe Lys Asp Leu Pro Asp Leu
        275                 280                 285

Lys Cys Pro Leu Thr Gly Gly Leu Leu Arg Gln Pro Val Lys Thr Ser
    290                 295                 300

Lys Cys Cys Asn Ile Asp Phe Ser Lys Glu Ala Leu Glu Asn Ala Leu
305                 310                 315                 320

Val Glu Ser Asp Phe Val Cys Pro Asn Cys Glu Thr Arg Asp Ile Leu
                325                 330                 335

Leu Asp Ser Leu Val Pro Asp Gln Asp Lys Glu Lys Glu Val Glu Thr
            340                 345                 350

Phe Leu Lys Lys Gln Glu Glu Leu His Gly Ser Ser Lys Asp Gly Asn
        355                 360                 365

Gln Pro Glu Thr Lys Lys Met Lys Leu Met Asp Pro Thr Gly Thr Ala
    370                 375                 380

Gly Leu Asn Asn Asn Thr Ser Leu Pro Thr Ser Val Asn Asn Gly Gly
385                 390                 395                 400

Thr Pro Val Pro Pro Val Pro Leu Pro Phe Gly Ile Pro Pro Phe Pro
                405                 410                 415

Met Phe Pro Met Pro Phe Met Pro Pro Thr Ala Thr Ile Thr Asn Pro
            420                 425                 430

His Gln Ala Asp Ala Ser Pro Lys Lys
        435                 440

<210> SEQ ID NO 7
<211> LENGTH: 35
<212> TYPE: DNA
<213> ORGANISM: Artificial Sequence
<220> FEATURE:
<223> OTHER INFORMATION: Synthetic Primer

<400> SEQUENCE: 7
```

```
cggaattcca tatggctgtc atatactata agttc                                    35

<210> SEQ ID NO 8
<211> LENGTH: 36
<212> TYPE: DNA
<213> ORGANISM: Artificial Sequence
<220> FEATURE:
<223> OTHER INFORMATION: Synthetic Primer

<400> SEQUENCE: 8
tttataatgc ggccgctcac ttttgattat tggtcg                                   36

<210> SEQ ID NO 9
<211> LENGTH: 30
<212> TYPE: DNA
<213> ORGANISM: Artificial Sequence
<220> FEATURE:
<223> OTHER INFORMATION: Synthetic Primer

<400> SEQUENCE: 9
cccaagctta tgagtagcac gatattttac                                          30

<210> SEQ ID NO 10
<211> LENGTH: 30
<212> TYPE: DNA
<213> ORGANISM: Artificial Sequence
<220> FEATURE:
<223> OTHER INFORMATION: Synthetic Primer

<400> SEQUENCE: 10
atcaagcttt catttcttag ggcttgcgtc                                          30

<210> SEQ ID NO 11
<211> LENGTH: 33
<212> TYPE: DNA
<213> ORGANISM: Artificial Sequence
<220> FEATURE:
<223> OTHER INFORMATION: Synthetic Primer

<400> SEQUENCE: 11
ctcaagctta tgtcgtcagt cgtctactat aag                                      33

<210> SEQ ID NO 12
<211> LENGTH: 33
<212> TYPE: DNA
<213> ORGANISM: Artificial Sequence
<220> FEATURE:
<223> OTHER INFORMATION: Synthetic Primer

<400> SEQUENCE: 12
gggaagcttc taattcttct tctggttatt gac                                      33

<210> SEQ ID NO 13
<211> LENGTH: 30
<212> TYPE: DNA
<213> ORGANISM: Artificial Sequence
<220> FEATURE:
<223> OTHER INFORMATION: Synthetic Primer

<400> SEQUENCE: 13
acggagctcg gtagattagt aaaggaaatc                                          30

<210> SEQ ID NO 14
<211> LENGTH: 30
<212> TYPE: DNA
<213> ORGANISM: Artificial Sequence
```

-continued

```
<220> FEATURE:
<223> OTHER INFORMATION: Synthetic Primer

<400> SEQUENCE: 14
tatgagctct agtgatcgtt aaaggtgacc                                30
```

GENES CONFERRING TOLERANCE TO ETHANOL AND HIGH TEMPERATURE FOR YEASTS

CROSS REFERENCE TO RELATED APPLICATIONS

This application is a divisional of U.S. patent application Ser. No. 14/358,876 filed on May 16, 2014, which is a 35 U.S.C. § 371 national phase entry of PCT application No. PCT/US2013/021100 filed Jan. 11, 2013, which claims priority to U.S. provisional application Nos. 61/585,873 and 61/585,917, filed Jan. 12, 2012.

TECHNICAL FIELD

The disclosure relates to genes that confer ethanol tolerance to yeasts used to produce ethanol by fermentation, in particular to increased ethanol tolerance of xylose fermenting strains of *H. polymorpha*, to ethanol sensitive mutants of *H. polymorpha* useful to identify ethanol tolerance genes, to ethanol tolerant recombinants of *H. polymorpha*, and more particularly to genetic sequences from *H. polymorpha* and *P. stipitis* herein designated HpETT1 and PsETT1, respectively, that are similar in sequence to the MPE1 gene of *S. cerevisiae* but that confer increased ethanol tolerance in yeasts including *H. polymorpha* and *S. cerevisiae*.

BACKGROUND

The references cited in this Background section and in the Description that follows are to provide a better understanding of the invention described herein after, as a resource for materials and methods that may further enable one to practice the methods and/or obtain the compositions later described herein, and as an abbreviation for such methods. Accordingly each reference cited herein is incorporated by reference to the extent the references provide a teaching that aids in the making and using of the invention later claimed. If there is any conflict in the disclosure provided herein and the cited references, the present disclosure controls over the teaching of the cited reference to the extent they conflict. The citation of a reference anywhere herein is not an admission that such a reference is pertinent to, or prior art to the invention claimed hereafter.

*Hansenula polymorpha* is a yeast species of both industrial and scientific importance. This non-conventional thermotolerant methylotrophic yeast is one of the best yeast systems for the production of heterologous proteins (Gellissen, 2000; Gellissen, (ed.). 2002; Suckow and Gellissen, 2002), it serves as a model to study peroxisome function (Van der Klei and Veenhuis, 2002), methanol metabolism, nitrate assimilation (Siverio, 2002) and stress responses (Ubiyvovk et al., 2006). *H. polymorpha* also has potential to be useful in biofuel production by fermentation of lignocellulosic carbon sources because it is able to ferment xylose (Ryabova et al., 2003), and is one of the most thermotolerant of yeast species (Guerra et al., 2005). However *H. polymorpha*'s utility as an organism to produce ethanol by fermentation may be limited because its growth is rather sensitive to ethanol in comparison to other yeasts, such as *S. cerevisiae*.

SUMMARY

The present inventors recognized that to be useful for commercial applications in biofuel production by fermentation, it would be desirable if the tolerance of *H. polymorpha* to ethanol could be improved. The discoveries described herein arose from research that focused on identification of target gene(s) for constructing ethanol tolerant strains of *H. polymorpha*. The inventors created a library collection of insertional mutants of *H. polymorpha*. From the collection of insertional mutants one transformant (herein designated 7E) was selected that was shown to be highly sensitive to ethanol. From sequencing the insertional cassette in this mutant it was discovered that the insertion disrupted an open reading frame of a gene herein designated HpETT1 (SEQ. ID NO: 1) encoding an unknown protein (SEQ. ID NO: 2) correspondingly designated Ett1. By comparing the amino acid sequence of Ett1 to yeast databases, it was discovered that Ett1 shares about 39% sequence identity with a protein of *Saccharomyces cerevisiae* (SEQ. ID NO: 5) encoded by the MPE1 gene (SEQ. ID NO: 6). This gene was reported to be an essential yeast gene that encodes a protein that is necessary for in vitro RNA 3'-end processing and is a subunit of the so-called CPF complex (Vo et al., 2001). The MPE1 gene is apparently essential for *S. cerevisiae* because a *S. cerevisiae* MPE1 deletion mutant is not viable.

In contrast, the *H. polymorpha* mutant 7E identified by the inventors remains viable despite having a disruption in a gene that has close ORF similarity to the *S. cerevisiae* MPE1 gene. Despite its viability on ordinary growth media, as noted above, the 7E mutant is hypersensitive to ethanol. As further demonstrated herein, expression of the undisrupted HpETT1 gene in the 7E mutant successfully complemented the mutant's hypersensitivity to ethanol.

Searching yeast databases revealed another homologous gene, herein designated PsETT1, present in the genome of another xylose fermenting yeast *Pichia stipitis*. The product of PsETT1, PsEtt1, has about 37% amino acid identity to HpEtt1. The inventors isolated and expressed the PsETT1 gene in the *H. polymorpha* 7E mutant and demonstrated that like HpETT1, expression of the *P. stipitis* gene at least partially complemented the *H. polymorpha* ett1 mutant's hypersensitivity to ethanol.

Still further, it is shown that overexpression of the native HpETT1 gene in *H. polymorpha* using a multi-copy integrant constructed such as described herein resulted in a transformed strain of *H. polymorpha* having about a 10-fold increase in tolerance to ethanol relative to the parent strain. More surprisingly still, it is shown that expression of the *H. polymorpha* HpETT1 gene in *S. cerevisiae* also conferred a detectable increase in ethanol tolerance in that yeast.

Accordingly, the present teaching presents several useful new aspects. One aspect is a mutant strain of *H. polymorpha* characterized as being ethanol sensitive and having a mutation that disrupts functional expression of the HpETT1 gene. Another aspect is a method of identifying a gene that confers ethanol tolerance in a yeast strain that includes transforming the *H. polymorpha* ett1 mutant strain with a vector that expresses a candidate nucleic acid, selecting a transformant that complements the ett1 mutant's sensitivity to ethanol, and identifying the sequence of the candidate nucleic acid to identify the gene that confers ethanol tolerance. Another aspect is an isolated nucleic acid encoding an Ett1 protein, which is characterized as a nucleic acid that when expressed in the ett1 mutant complements the ethanol sensitivity of that mutant. Representative examples of nucleic acids encoding Ett1 proteins are the HpETT1 gene of SEQ.ID NO: 1 that encodes the HpEtt1 protein of SEQ.ID NO:2 and the PsETT1 gene of SEQ. ID NO: 3 that encodes the PsEtt1 protein of SEQ.ID.NO: 4. A related aspect is identification of a new type of protein class designated Ett1 and isolated versions of the same. Still another related aspect is a recombinant nucleic acid comprising a sequence that encodes an Ett1 protein and a promoter that is operable in a selected yeast strain operably configured to express the ETT1 gene in the selected yeast strain. Examples of such vectors are illustrated in FIG. 1 and include p21+ETT1Hp and pGLG61+ETT1Hp each configured to express the *H. polymorpha* Ett1 protein and p70+ETT1Pst that is configured to express a *P. stipitis* Ett1 protein. These vectors have promoters selected to be particularly operable in *H. polymorpha*. Another example is prPGK1Sc+ETT1Hp which are configured to express the HpETT1 gene in *S. cerevisiae*.

Another important aspect is yeast strains having enhanced ethanol tolerance that can be produced by overexpressing an Ett1 protein in the yeast strain. The yeast strain with increased ethanol tolerance can be a *H. polymorpha* strain, a *S. cerevisiae* strain or a *P. stipitis* strain comprising a recombinant nucleic acid that overexpresses at least one of the Ett1 proteins from *H. polymorpha* or *P. stipitis*. Exemplary embodiments of such strains include *H. polymorpha* strains 7E-GAPDHETT1Pst, 7E-GAPDHETT1Hp, and 3Leu+pETT1-10 and *S. cerevisiae* strain BY4742+ prPGK1Sc+ETT1Hp.

It should be noted that initially the nomenclature for the vectors, genes, proteins and strains used in the materials and methods section had the root term "MPE1", followed by a suffix for the organism from which the gene was obtained, i.e., Hp for *H. polymorpha*, Pst for *P. stipitis*, and Sc, for *S. cerevisiae*. This nomenclature was originally used because after searching yeast databases for sequences that were similar to the gene disrupted in the *H. polymorpha* 7E mutant, it was discovered that the closest known sequence was the *S. cerevisiae* MPE1 gene, therefore the closest similar sequences from *P. stipitis* and *H. polymorpha* were originally given the same name. However, it being now discovered that the *S. cerevisiae* MPE1 gene does not complement the ethanol sensitivity of the *H. polymorpha* 7E mutant, while the similar sequences from *H. polymorpha* and *P. stipitis*, do complement the mutation, it is more appropriate to refer to the *H. polymorpha* and *P. stipitis* genes as a new type of ethanol tolerance genes denominated herein with the suffix "ETT1." Accordingly, the vectors initially denominated as p21+MPE1Hp and pGLG61+ MPE1Hp or p70+MPE1 Pst were renamed as p21+HpETT1 and pGLG61+HpETT1 and p70+PsETT1. Only the *S. cerevisiae* gene is referred to strictly as MPE1.

BRIEF DESCRIPTION OF THE DRAWINGS

FIG. 4 illustrates a genomic integrant and probe for identification of plasmid chromosomal integrant.

FIG. 5 illustrates a Southern blot for assaying copy number of integrants 7E, N1 and N2.

FIG. 6 shows a sequence comparison between the *H. polymorpha* HpEtt1 protein (Hp), *S. cerevisiae* Mpe1 protein (Sc), *P. stipitis* PsEtt1 protein (Ps) and the consensus sequences between them.

DETAILED DESCRIPTION

Definitions

Figure 1A:
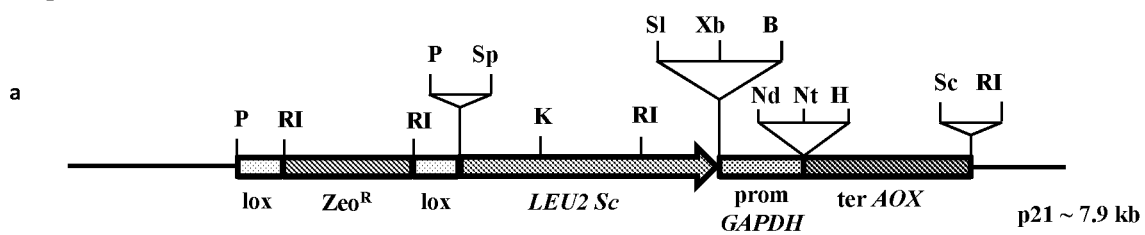
FIG. 1a shows schematic representations of vectors described herein. This Figure shows a *H. polymorpha* expression vector.

Certain common or newly introduced terms that have been used herein are believed to be commonly understood to those of ordinary skilled in the art, or would be commonly understood in view of the present disclosure. Such commonly understood meanings are embraced herein, however, to resolve any questions of clarity that may be asserted by use of certain terms, the following non-limiting definitions are provided to assist in better understanding the present invention.

A sibling strain, is one strain of microorganism that is of the same species as another strain although not necessarily of the same genotype.

A parental strain, is a strain of microorganism that has the same genetic background as a derivative strain of the same microorganism, except for alterations that have been made in the derivative strain.

An ett1 mutant strain, is a strain of H. polymorpha, exemplified herein by H. polymorpha 7E, having a mutation that disrupts the expression of the gene identified herein as HpETT1 and which shows sensitivity to growth on ethanol in comparison to a sibling or parental H. polymorpha strain lacking the mutation.

An ETT1 gene is a gene from any source that encodes a protein (Ett1 protein) that when expressed in an ett1 mutant strain, at least partially overcomes the ethanol sensitive growth properties of the mutant strain.

A HpETT1 gene is a nucleic acid obtained from a strain of H. polymorpha that encodes an Ett1 protein, exemplified herein by SEQ. ID NO 1 for the gene and SEQ. ID NO 2 for the protein (HpEtt1 protein).

A PsETT1 gene is a nucleic acid obtained from a strain of P. stipitis that encodes an Ett1 protein, exemplified herein by SEQ. ID NO 3 for the gene and SEQ. ID NO 4 for the protein (PsEtt1 protein).

Overexpress, means to genetically express a nucleic acid encoding an ORF in a transformed host cell to a greater agree than the same nucleic acid is expressed in a non-transformed parent of the host cell under similar growth conditions.

Increased ethanol sensitivity or ethanol sensitive growth means that that when ethanol is present in a growth medium, a subject strain grows at a slower rate, to a lower density, or otherwise with decreased vigor in comparison to a sibling strain of the same organism grown on the same media.

Enhanced ethanol tolerance means that when ethanol is present in a growth medium, a subject strain grows at a faster rate, to a greater density, or otherwise with increased vigor in comparison to a sibling strain of the same organism grown on the same media.

Materials and Methods Used to Make Exemplary Embodiments

Strains and Growth Condition.

The yeast strains disclosed herein are listed in Table 1. The H. polymorpha NCYC495 leu1-1 strain was used as a recipient for insertional mutagenesis and was maintained on minimal medium containing 0.67% YNB (Difco, Detroit, Mich., USA) supplemented with 2% sucrose and leucine at 40 mg $L^{-1}$ at 37° C. H. polymorpha 7E was selected as an insertional mutant of H. polymorpha NCYC495 leu1-1 strain that is unable to grow on YPS medium (0.5% yeast extract, 1% peptone and 2% sucrose) supplemented with 7% ethanol.

The H. polymorpha CBS4732s strain (Lahtchev et al., 2002) was used as a source of the HpETT1 gene. The strain was maintained on YPD medium (0.5% yeast extract, 1% peptone and 2% glucose) at 37° C.

The Pichia stipitis strain CBS6054 (Yang et al., 1994) was used as the source of the P. stipitis PsETT1 gene, which is an orthologue of HpETT1. S. cerevisiae strain BY4742 (Brachmann et al., 1998) was used as the source for the S. cerevisiae MPE1 gene.

The 3Leu+ strain (Ishchuk et al., 2008) was used as a recipient strain for HpETT 1 overexpression in H. polymorpha.

Yeast transformants were selected either on YNB medium with 2% sucrose or on YPS medium (0.5% yeast extract, 1% peptone and 2% sucrose) supplemented with geneticin at 1 g $L^{-1}$ or zeocin at 140 mg $L^{-1}$.

The Escherichia coli strain DH5α[Φ80dlacZΔM15, recA1, endA1, gyrA96, thi-1 hsdR17 ($r_K^-$, $m_K^+$), supE44, relA1, deoR, Δ(lacZYA-argF) U169] was used in experiments which required a bacterial host. The bacterial strain was grown at 37° C. in the rich (LB) medium as described in Sambrook et al., 1989. Transformed E. coli cells were maintained on a medium containing 100 mg $L^{-1}$ of ampicillin.

TABLE 1

Yeast strains used in this study

| Strain | Description | Reference |
| --- | --- | --- |
| H. polymorpha:<br>NCYC495<br>leu1-1 | leu2 | Gleeson and Sudbery, 1988 |
| 7E | NCYC495 leu1-1 insertional mutant, leucine prototroph | this study |

TABLE 1-continued

Yeast strains used in this study

| Strain | Description | Reference |
| --- | --- | --- |
| CBS4732s | leu2 | Lahtchev et al., 2002 |
| 3Leu+ | NCYC495 leu1-1 derivative, leucine prototroph | Ishchuk et al., 2008 |
| P. stipitis CBS6054 | wild-type | Yang et al., 1994 |
| S. cerevisiae BY4742 | MATα his3_1 leu2_0 lys2_0 ura3_0 | Brachmann et al., 1998 |

Construction of Plasmids

Two integrative plasmid vectors p21 and p70 (FIG. 1a, FIG. 1b) were constructed for use as the *H. polymorpha* integration and expression cassette. Each plasmid contains the strong *H. polymorpha* constitutive promoter for glyceraldehyde 3-phosphate dehydrogenase gene (GAPDH) and the terminator of alcohol oxidase (AOX). The plasmids p21 and p70 are the derivatives of p19L2 (Voronovsky et al., 2002) and differ only slightly in the restriction sites available for cloning of the subject gene to be expressed.

Figure 1B:
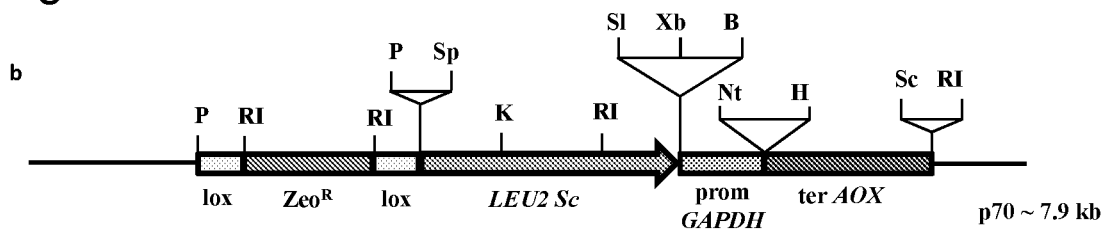
FIG. 1b also shows schematic representations of vectors described herein. This Figure also shows a *H. polymorpha* expression vector.
Figure 1C:
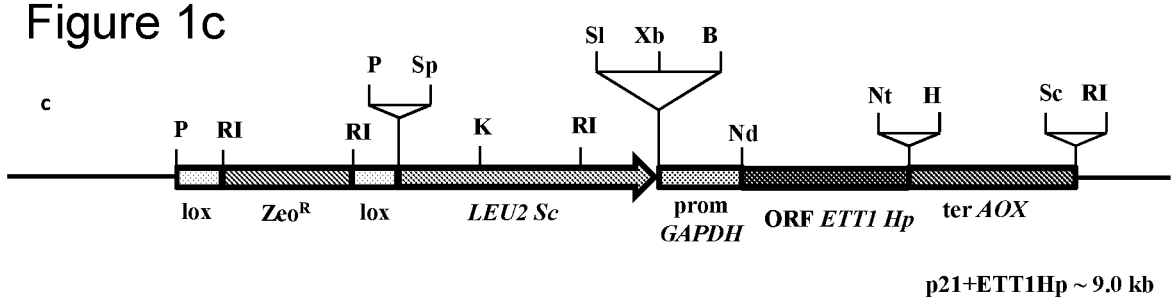
FIG. 1c shows the construct used for expressing the *H. polymorpha* HpETT1 gene.

Based on the initial discovery that the *H. polymorpha* 7E insertional mutant contained an interruption of a gene having an open reading frame with about 39% identity with the *S. cerevisiae* MPE1 gene we sought to obtain the natural *H. polymorpha* homologue of MPE1. The resulting construct was plasmid p21+ETT1Hp (FIG. 1c) which is based on the p21 plasmid cassette (FIG. 1a). The genomic DNA isolated from *H. polymorpha* CBS4732s strain served as a template to obtain theMPE1 homologue herein designated HpETT1, which was obtained by amplification of the genomic DNA containing the open reading frame using the primers

```
IS202
                                            (SEQ. ID NO: 7)
(5'-CGGAATTCCATATGGCTGTCATATACTATAAGTTC-3')
and IS203
                                            (SEQ. ID NO: 8)
(5'-TTTATAATGCGGCCGCTCACTTTTGATTATTGGTCG-3').
```

The PCR fragment was treated with restriction endonucleases NdeI and NotI at the underlined restriction sites and cloned into NdeI/NotI-linearized plasmid p21.

Figure 2A:
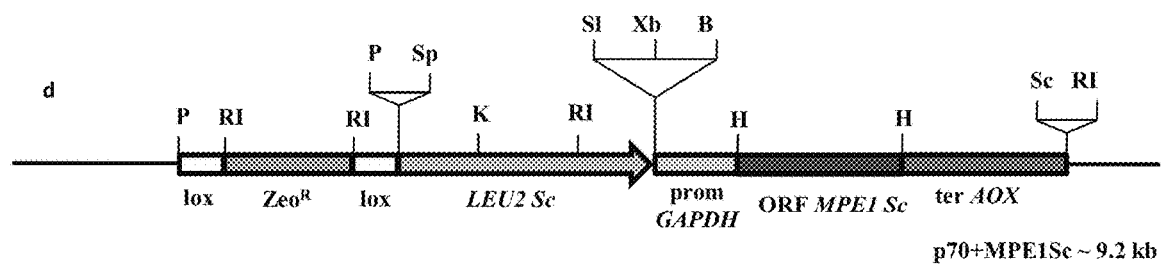
FIG. 2 also shows schematic representations of vectors described herein. 2a and 2b show the constructs for expressing the *S. cerevisiae* MPE1 gene and the *P. stipites* PsETT1 gene in *H. polymorpha*, respectively. 2c shows a vector for multicopy integration of the HpETT1 gene in *H. polymorpha*.
Figure 2B:
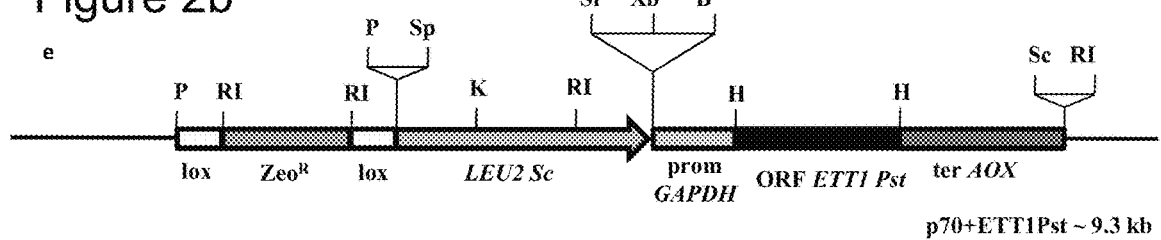
Figure 2C:
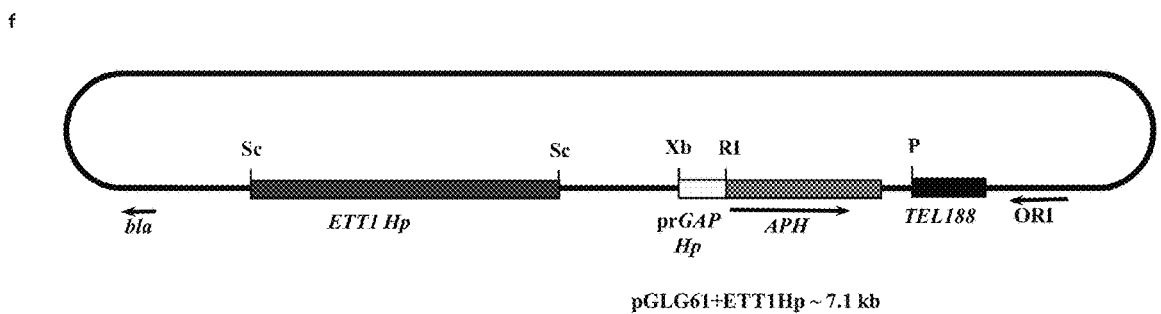

The genes homologous to HpETT1 were isolated from *S. cerevisiae* and *P. stipitis* and subcloned into the p70 expression cassette (FIG. 1b) resulting in the constructs p70+MPE1Sc and p70+ETT1Pst (FIG. 2a, FIG. 2b). The genomic DNA isolated from *S. cerevisiae* BY4742 and *P. stipitis* CBS6054 served as templates to amplify the open reading frames of *S. cerevisiae* MPE1 and PsETT1 geneS. For *S. cerevisiae* MPE1 the ORF primer pairs used were: IS249 (5'-CCCAAGCTTATGAGTAGCACGATATTTTAC-3') (SEQ. ID NO: 9) and IS250 (5'-ATCAAGCTTTCATTTCTTAGGGCTTGCGTC-3') (SEQ. ID NO: 10) for *P. stipitis*, the ORF primer pair used were: IS212 (5'-CTCAAGCTTATGTCGTCAGTCGTCTACTATAAG-3') (SEQ. ID NO: 11) and IS213 (5'-GGGAAGCTTCTAATTCTTCTTCTGGTTATTGAC-3') (SEQ. ID NO: 12). The corresponding PCR fragments were treated with endonuclease HindIII at the underlined restriction site and cloned into HindIII-linearized plasmid p70.

Another plasmid for expression of the HpETT1 gene constructed was pGLG61+ETT1Hp (FIG. 2f), which is a derivative of plasmid vector pGLG61 (Sohn et al., 1999). The pGLG61 vector promotes multi-copy-number integration of plasmid tandem repeats into the genome. The *H. polymorpha* HpETT1 gene was amplified from the genomic DNA of *H. polymorpha* CBS4732s strain using primer pair: IS206 (5'-ACGGAGCTCGGTAGATTAGTAAAGGAAATC-3') (SEQ. ID NO: 13) and IS207 (5'-TATGAGCTCTAGTGATCGTTAAAGGTGACC-3') (SEQ. ID NO: 14). The PCR fragment was treated with restriction endonuclease SacI at the underlined restriction site and ligated with 4.97 kb SacI-fragment of pGLG61.

Molecular Biology Techniques

Plasmid DNA isolations from *E. coli* were carried out by using NucleoSpin® Plasmid QuickPure (Macherey-Nagel, Germany). Taq DNA polymerase and Vent$_R$® DNA polymerase (both New England Biolabs, USA) were used for analytical and preparative PCR, respectively. T4 DNA ligase, T4 DNA polymerase and restriction enzymes were purchased from Fermentas, Lithuania.

Preparations of total DNA from yeast species were carried out by using DNeasy® Tissue Kit (Qiagen, Germany).

Transformation of *H. polymorpha* was performed by electroporation as described previously (Faber et al., 1994).

Southern blotting analysis was performed using the Amersham ECL Direct Nucleic Acid Labelling and Detection System (GE Healthcare, USA).

Recombinant Proteins

The HpEtt1 protein encoded by the HpETT1 gene of *H. polymorpha* with a sequence of 373 amino acids was expressed as His$_6$ fusion peptide after being cloned into pET-32-ac (+) (Novagen). The recombinant polypeptide was produced in *E. coli* BL21(DE3) and purified on nickel-nitriloacetic acid agarose (Qiagen) according to the manufacturer's instructions.

Illustrative Results

Isolation of *H. polymorpha* 7E Mutant

Figure 3A:
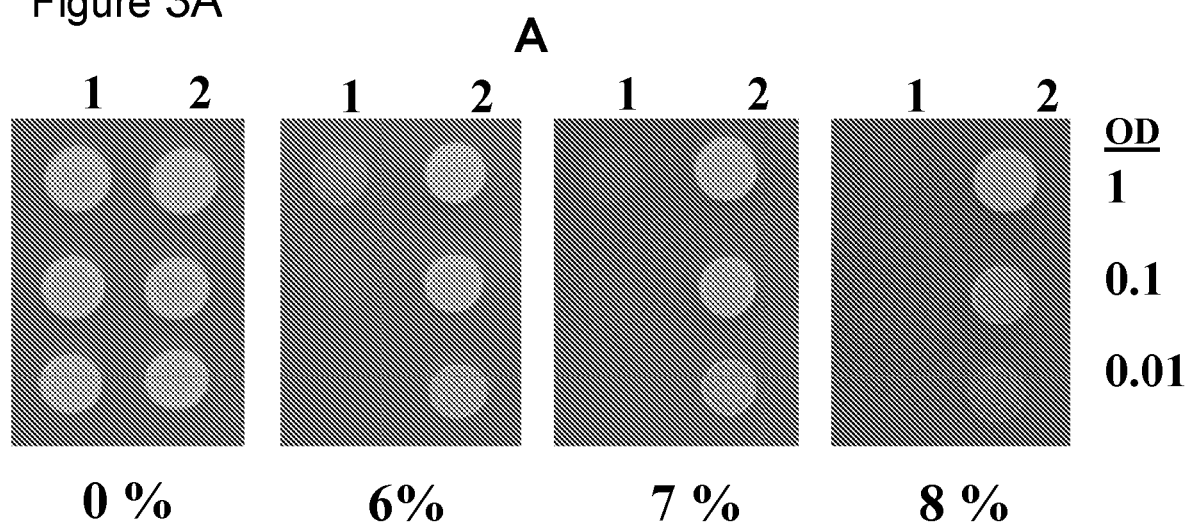
FIG. 3a depicts solid media density assays showing ethanol sensitivity for the HpETT1 mutant H polymorpha strain 7E (1) in comparison to non-mutant strains 3Leu+ (2) and parental strain NCYC495leu1-1 (3). This panel illustrates the densities after overnight growth at 37° C. of cells initially plated at the indicated optical densities on YNB media plus 2% sucrose with the indicated percentage of ethanol.

The parental *H. polymorpha* NCYC495 leu1-1 strain tolerates ethanol concentrations in the medium up to 7-8%. However, insertional mutant 7E was selected among *H. polymorpha* NCYC495 leu1-1 insertional transformants as a one unable to grow on the YNB medium supplemented with 7% ethanol. For this purpose the p19L2 plasmid (Voronovsky et al., 2002) linearized with BamHI was used as an insertional cassette. Leu+ transformants were replica-plated on the ethanol supplemented medium and screened for the growtH. Among 200 transformants only one was unable to grow on the 7% ethanol (designated 7E). The 7E mutant proved to be approximately 300-500 times more sensitive to ethanol compared to the control parental strain (3Leu+ transformant) (FIG. 3A). Unlike the recipient strain, the 7E mutant does not tolerate the stress ethanol concentration, but it does grow on the 1% ethanol as a sole carbon source (FIG. 3B) meaning it lacks any defects in ethanol utilization but is sensitive to ethanol concentrations at stress levels.

Figure 3B:
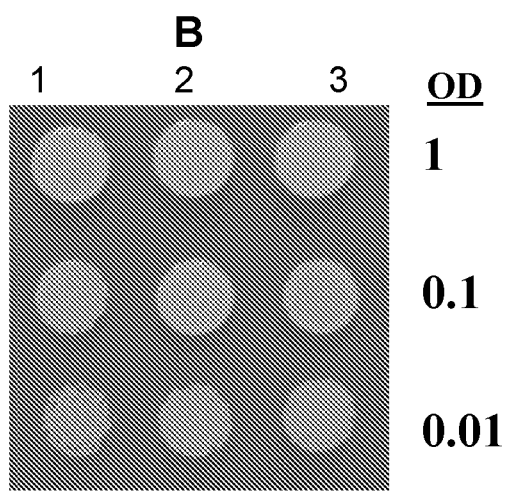
FIG. 3B illustrates the densities after overnight growth on YNB media in the presence of 1% ethanol.

Plasmid p19L2 carries the LEU2 gene of *S. cerevisiae* and when it is used to transform a *H. polymorpha* strain, 1 to a few copies of the plasmid might be integrated into the genome of *H. polymorpha*. For this reason the copy number of the insertional cassette in the genome of 7E mutant was estimated. The genomic DNA of the 7E mutant and a few other randomly selected Leu$^+$ transformants were treated with HindIII and probed with an ECL-labeled PCR fragment carrying the *S. cerevisiae* LEU2 gene. There is no HindIII site within LEU2 gene so one Southern blotting signal corresponds to one p19L2 copy in the genome (FIG. 3B). It was shown that the 7E mutant carried only one copy of insertional cassette integrated into the genome whereas transformants N1 and N2 gave 3 signals corresponding to 3 plasmids copies being integrated.

The 7E Insertional Mutant of *H. polymorpha* has a Disrupted Gene Homologous to the *S. cerevisiae* MPE1 Gene The genomic region flanking the insertional cassette in the 7E mutant was sequenced. It was shown that the plasmid disrupted the *H. polymorpha* open reading frame having 39% identity to protein (SEQ. ID NO: 6) encoded by the *S. cerevisiae* MPE1 gene (SEQ. ID NO: 5) which is annotated as coding an essential component of a cleavage and polyadenylation factor required for cleavage and polyadenylation of mRNA (Vo et al., 2001). A sequence comparison (FIG. 4) for sequences similar to the to *S. cerevisiae* MPE1 gene motifs identified by Vo et al., 2001 revealed that the *H. polymorpha* MPE1 like ORF (i.e., the HpETT1 gene) contains a zinc knuckle-like motif ($CX_2CX_5HX_4C$) between amino acids 168 and 182; a cysteine-rich B domain resembling RING finger between amino acids 266 and 319; and a region from amino acids 4 and 79 with high homology to the so called "A domain" identified in the *S. cerevisiae* homologue (FIG. 4) The insertional cassette in the 7E mutant disrupted the *H. polymorpha* HpETT1 gene by integration at a position 671 bp downstream of the start codon.

Not *S. cerevisiae* but *P. stipitis* ETT1 Gene Complement the ett1 Mutation in *H. Polymorpha*.

To study the functional complementation of ett1 mutation of *H. polymorpha* two heterologous homologues were chosen: the *S. cerevisiae* MPE1 gene and the gene from *P. stipitis* (another xylose fermenting yeast species) herein designated PsETT1. The putative product of PsETT1 discovered to have about 37% amino acid identity with the HpEtt1 protein. The effect of expressing these heterologous genes was compared with the expression of the *H. polymorpha* HpETT1 gene a as a control. For this purpose the 7E mutant was transformed with plasmids p70+MPE1Sc, p70+ETT1Pst and pGLG61+ETT1Hp (FIGS. 1.1-1.2). There it was shown that *S. cerevisiae* MPE1 gene did not restore the growth on the medium supplemented with 7% ethanol (FIG. 5). On the other hand, expression of the *P. stipitis* PsETT1 gene in the 7E mutant resulted in partial restoration of ethanol tolerance. The corresponding transformant 7E-GAPDHETT1Pst could grow on the medium with 7% ethanol although the growth was poor compared to those of the 3Leu+ and 7E-pETT1Hp-1 strains (FIG. 5). These data demonstrate that the genes of *H. polymorpha* and *P. stipitis* that are homologues of the MPE1 gene of *S. cerevisiae* are involved in ethanol tolerance. Accordingly the *H. polymorpha* and *P. stipitis* genes are hereby given the suffix designation "ETT1" for ethanol tolerance to distinguish them from MPE1 of *S. cerevisiae*. Another distinction is that expression of the *S. cerevisiae* MPE1 gene in *S. cerevisiae* is essential because a *S. cerevisiae* mutant in that gene is not viable, whereas in contrast, the *H. polymorpha* ett1 7E mutant isolated in herein is viable, although highly sensitive to exogenous ethanol.

Although the HpETT1 gene appears to be not essential for growth for *H. polymorpha*, the presence of RNA-binding zinc knuckle domain in the HpETT1 gene suggest a possible involvement in RNA maturation, which may be one of the processes negatively affected by ethanol exposure in this and other organisms.

Construction of *H. polymorpha* Strain Overexpressing Native HpETT1 Gene.

Figure 6:
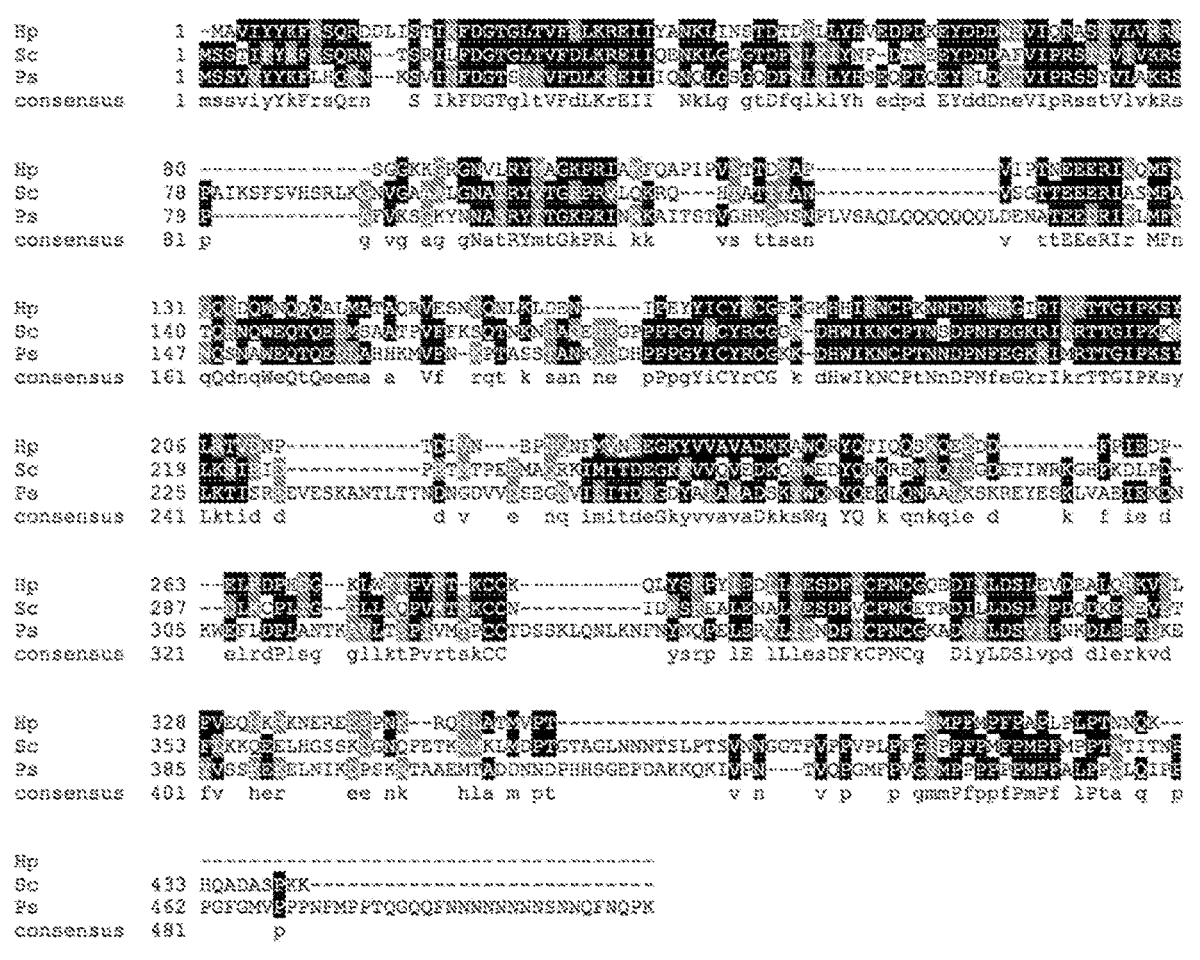

The *H. polymorpha* 3Leu+ strain (Ishchuk et al., 2008) was transformed with plasmid vector pGLG61+ETT1Hp (FIG. 1f) for overexpressing the HpETT1 gene in *H. polymorpha*. Being a pGLG61 (Sohn et al., 1999) derivative the corresponding plasmid vector contains the telomeric sequence and the bacterial aminoglycoside 3-phosphotransferase (APH, genetecin resistance) gene. This vector promotes multicopy integration of plasmid tandem repeats into the genome (Sohn et al., 1999). The collection of geneticin resistant transformants was screened for improved ethanol resistance. The ethanol resistance varied among the transformants. This could be explained by different copy number of the plasmid integrated into the genome. The transformant 3Leu+pETT1-10 proved to be approximately 10-fold more tolerant to exogenous ethanol compared to the recipient parent strain 3Leu+ (FIG. 6). The copy number of the HpETT1 gene in the transformant was estimated by Southern blotting (FIG. 3B). Comparing the intensity of the signal to the 3Leu+ strain which contains only one copy of the HpETT1 gene, it was determined that the 3Leu+pETT1-10 transformant carries approximately 6-7 copies in its genome.

The *H. polymorpha* HpETT1 Multicopy Integrant has Improved Growth on the Medium with Ethanol.

Figure 7:
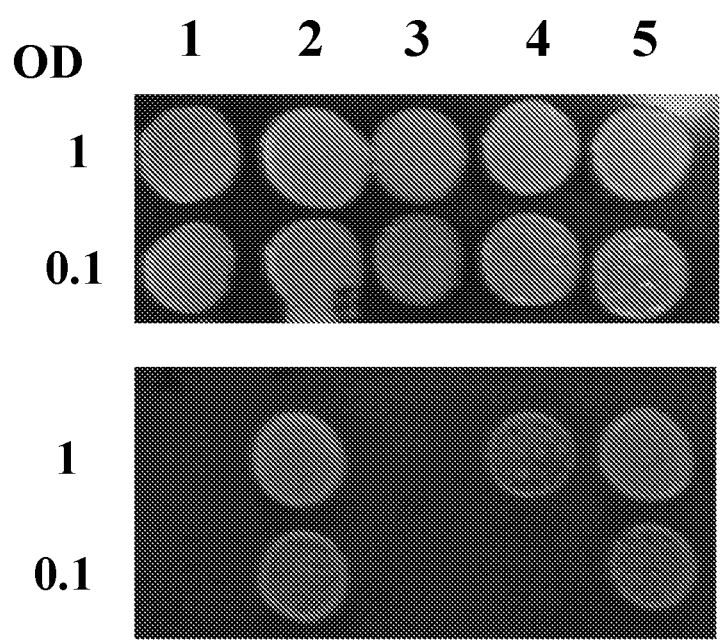
FIG. 7 depicts a solid media density assay showing complementation of the *H. polymorpha* 7E mutation by expression of the HpETT1 and PsETT1 genes but not the *S. cerevisiae* MPE1 gene. The upper panel shows growth on YPD medium alone and the lower panel shows growth on the same plus 7% ethanol. The strains are: (1) the *H. polymorpha* 7E mutant parental strain; (2) the 3Leu+ control; (3) the 7E transformant designated 7E GAPDHMPE1Sc transformed with the *S. cerevisiae* MPE1 gene; (4) the 7E transformant designated 7E-GAPDHETT1Pst transformed with the *P. sapiles* ETT1 gene; and (5) the 7E transformant designated 7E-pETT1HP-1 transformed with the *H. polymorpha* ETT1 gene.
Figure 8:
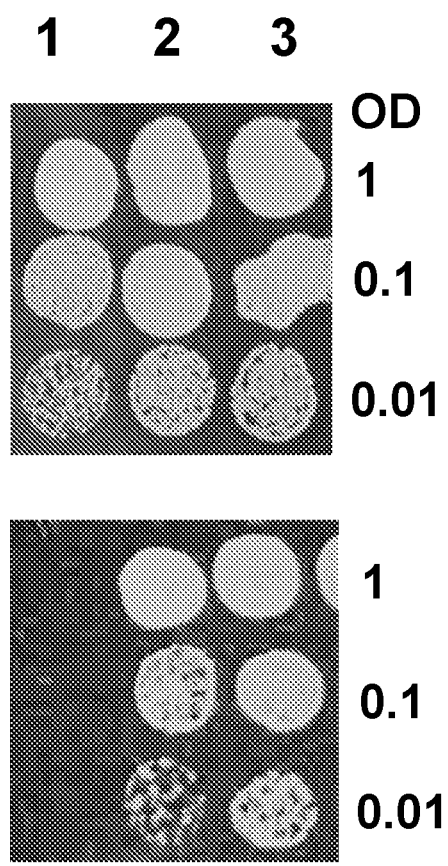
FIG. 8 depicts a solid media density assay showing enhanced ethanol tolerance in the strain 3Leu+pETT1-10 overexpressing the HpETT1 gene. The 3Leu+pETT1-10 strain was obtained by transformation of 3Leu+ strain with the multicopy integration vector pGLG61+ETT1HP. The upper panel shows growth on YPS media alone and the lower panel shows growth on the same plus 7% ethanol The strains are: (1) the 7E mutant; (2) the 3Leu+ control parent strain; and (3) the 3Leu+pETT1-10 strain, which is the control parent transformed with multiple copies of the *H. polymorpha* pETT1 gene.

Tolerance of *H. polymorpha* strains to ethanol was measured as the viability in the presence of ethanol in liquid YPD/YPS media. In the media without ethanol there was no difference between strains growth (FIG. 7A, FIG. 8A). The 3Leu+pETT1-10 transformant had improved growth on both 6% and 7% ethanol media (FIG. 7B, FIG. 8B). At cultivation time of 48 and 72 hours the growth density of the multicopy HpETT1 integrant was 2-fold higher than the 3Leu+ strain in the 6% ethanol medial. Under conditions of cultivation in 7% ethanol medium (FIG. 8B) a difference in growth rate and density was observed within the first day of incubation and was 3.4 times higher for the 3Leu+pETT1-10 transformant compared to the parent recipient strain 3Leu+. However, during prolonged cultivation (48, 72 and 96 hours) all strains exhibited a decline in growth, although the growth kinetics of the HpETT1 multicopy integrant was observably better throughout the cultivation period. As noted before, the 7E mutant which is hypersensitive to ethanol, showed impaired growth on the 7% ethanol medium.

The *H. polymorpha* ETT1 Multi-Copy Integrant is Resistant to Other Kinds of Stress.

Figure 9:
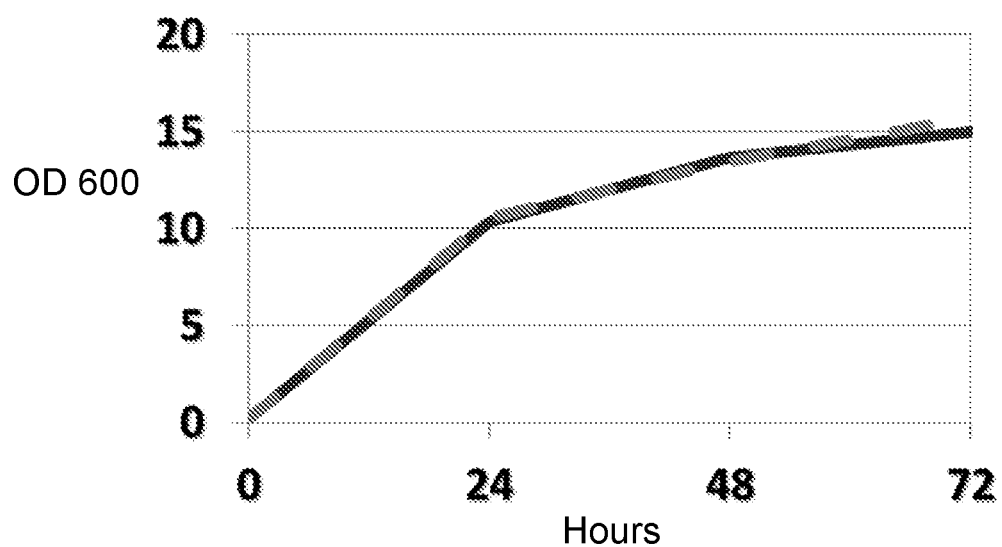
FIG. 9 is a graph showing enhanced ethanol tolerance in growth characteristics of strain 3leu+pETT1-10 overexpressing the HpETT1 gene in *H. polymorpha* (dotted lines) in comparison to the control strain 3Leu+ (solid lines) when grown in YPD medium lacking ethanol.
Figure 10:
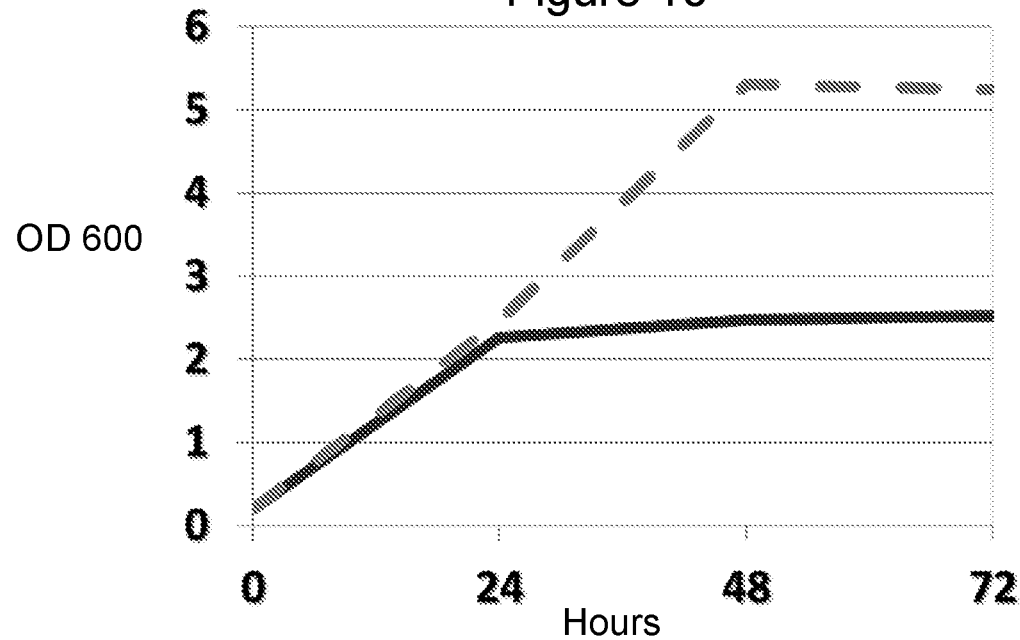
FIG. 10 is a graph showing enhanced ethanol tolerance in growth characteristics of strain 3leu+pETT1-10 overexpressing the HpETT1 gene in *H. polymorpha* (dotted lines) in comparison to the control strain 3Leu+ (solid lines) when grown in YPD medium containing 6% ethanol.
Figure 11:
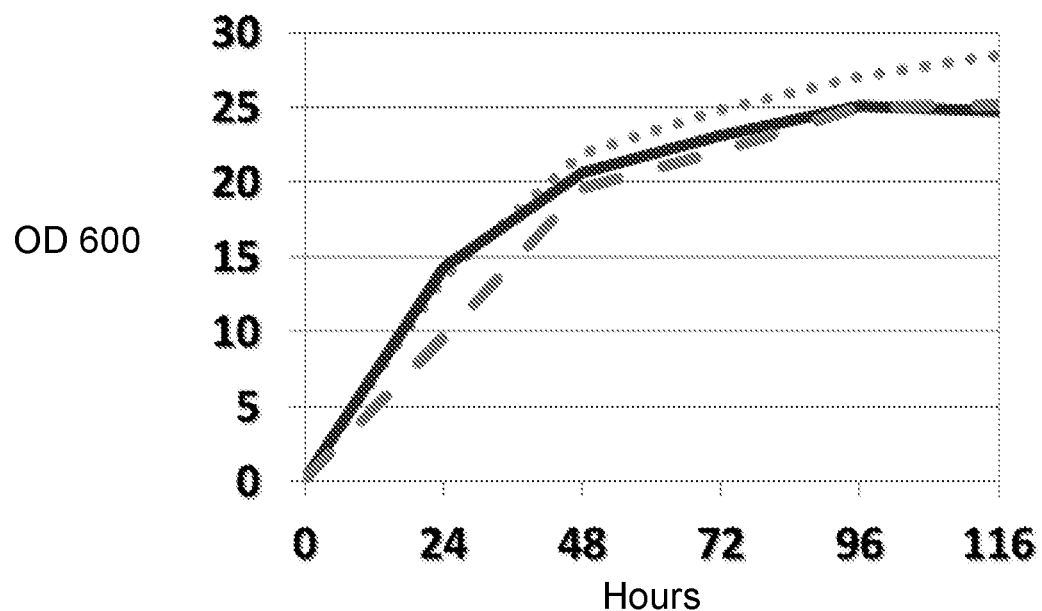
FIG. 11 is a graph showing ethanol sensitivity of the 7E mutant (dotted lines) and enhanced ethanol tolerance in growth characteristics of strain 3Leu+pETT1-10 (dashed lines) overexpressing the HpETT1 gene in *H. polymorpha* in comparison to the control parent strain 3leu+ (solid lines) on YPS medium alone.
Figure 13:
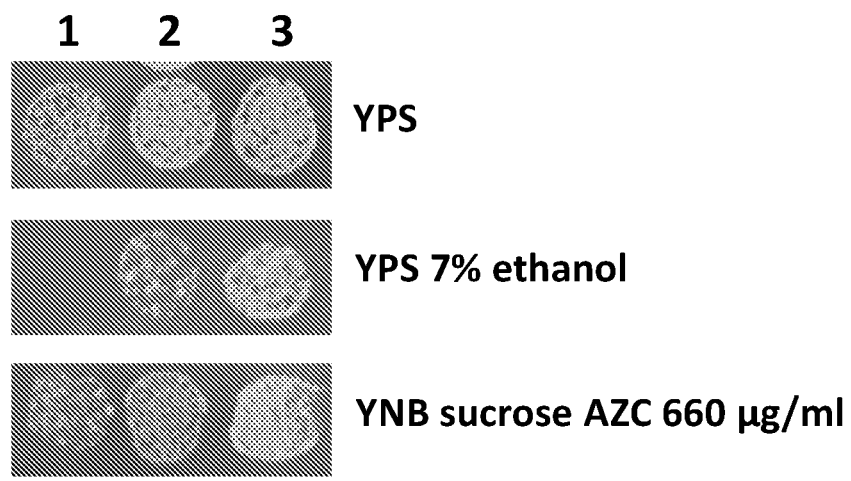
FIG. 13 shows increased stress tolerance in the 3Leu+ pETT1-10 (3) strain overexpressing the HpETT1 gene by growth on solid media with and without ethanol or the stress inducing agent AZC in comparison to the parent control strain 3eu+ (2) and the mutant strain 7E strain (1).

The 3Leu+pETT1-10 transformant is also more resistant to the proline analogue 2-azetidine carboxylic acid, AZC (FIG. 9) than the parent recipient strain. AZC is incorporated into proteins competitively with proline and results in protein misfolding (Lane et al., 1971; Zagari et al., 1990), and this compound is known to induce the expression of heat-shock proteins. Thus the effect of AZC treatment is a stress response that resembles that of heat-shock (Trotter et al., 2002). This likely explains why the 7E mutant does not grow well at 50° C. compared to the 3Leu+ parent strain (FIG. 10, FIG. 11). Further evidence that the product of the HpETT1 is related to a heat shock response is that the 3Leu+pETT1-10 transformant that overexpresses HpETT1 displays slightly improved growth at 50° C. comparing to the 3Leu+ strain (FIG. 11) and is more tolerant to heat-shock (FIG. 13).

Overexpression of the *H. polymorpha* HpETT1 Gene in *S. cerevisiae* Increases Ethanol Tolerance.

Figure 12:
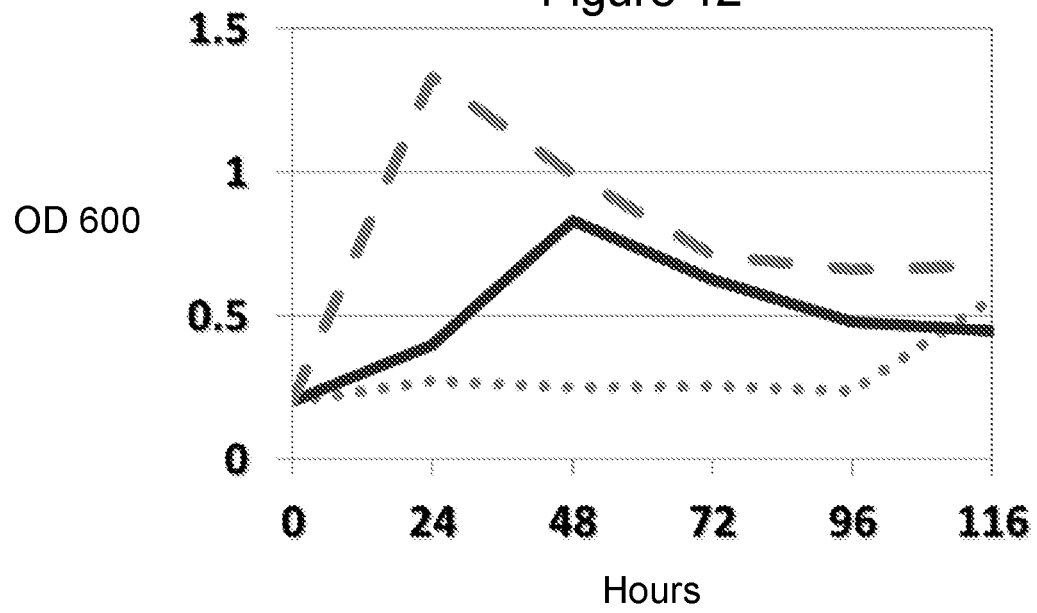
FIG. 12 is a graph showing ethanol sensitivity of the 7E mutant (dotted lines) and enhanced ethanol tolerance in growth characteristics of strain 3Leu+pETT1-10 (dashed lines) overexpressing the HpETT1 gene in *H. polymorpha* in comparison to the control parent strain 3leu+ (solid lines) on YPS medium containing 7% ethanol.

The *H. polymorpha* HpETT1 gene was cloned into a yeast expression vector under control of the *S. cerevisiae* PGK1 promoter. Two transformants showed slightly increased growth on ethanol media (FIG. 12). As with the case of expression in *H. polymorpha* increased ethanol tolerance will likely be observed when *S. cerevisiae* is transformed with the expression vector in high-copy number.

Purification of *H. polymorpha* HpEtt1 Protein.

Figure 14:
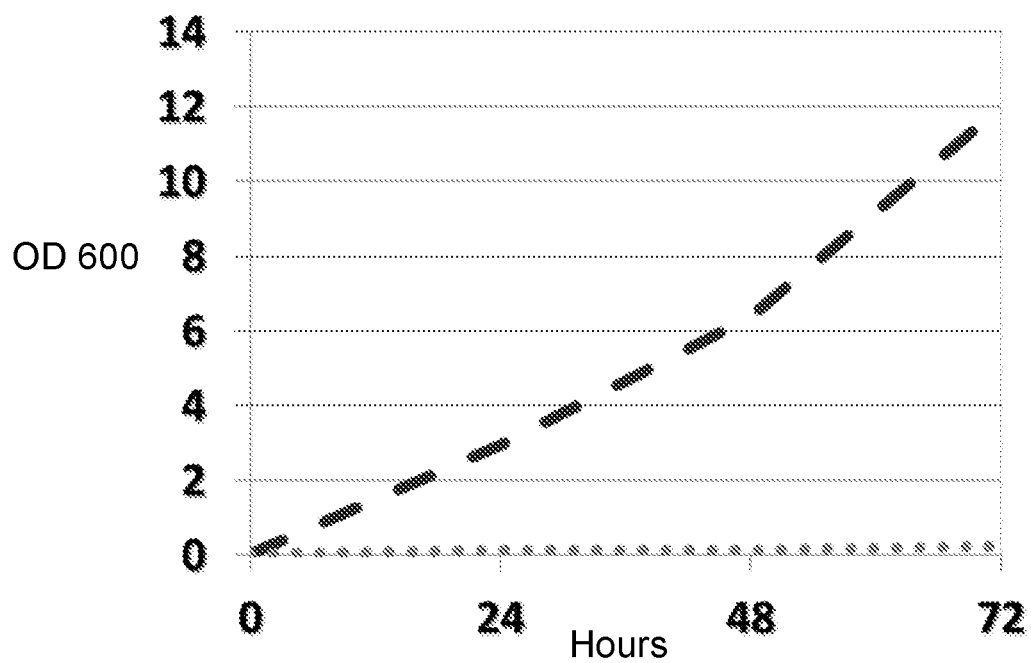
FIG. 14 is a graph depicting temperature sensitivity of the H. polymorpha 7E mutant (dashed line) in comparison with its parental strain 3leu+ (solid line).
Figure 15:
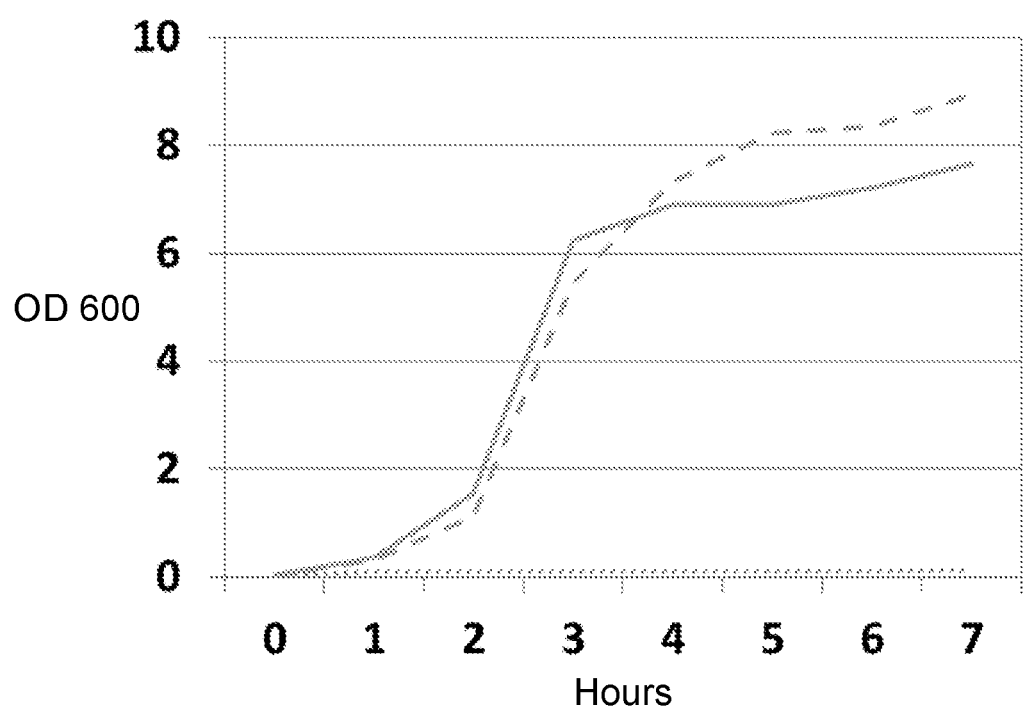
FIG. 15 is a graph showing improved growth characteristics of the strain 3Leu+pETT1-10 overexpressing the HpETT1 gene (dashed line) when grown in YNB media using 2% xylose as the carbon source at 50° C. in comparison to the 7E mutant (dotted line) and the parental strain 3leu+ (solid line).
Figure 16:
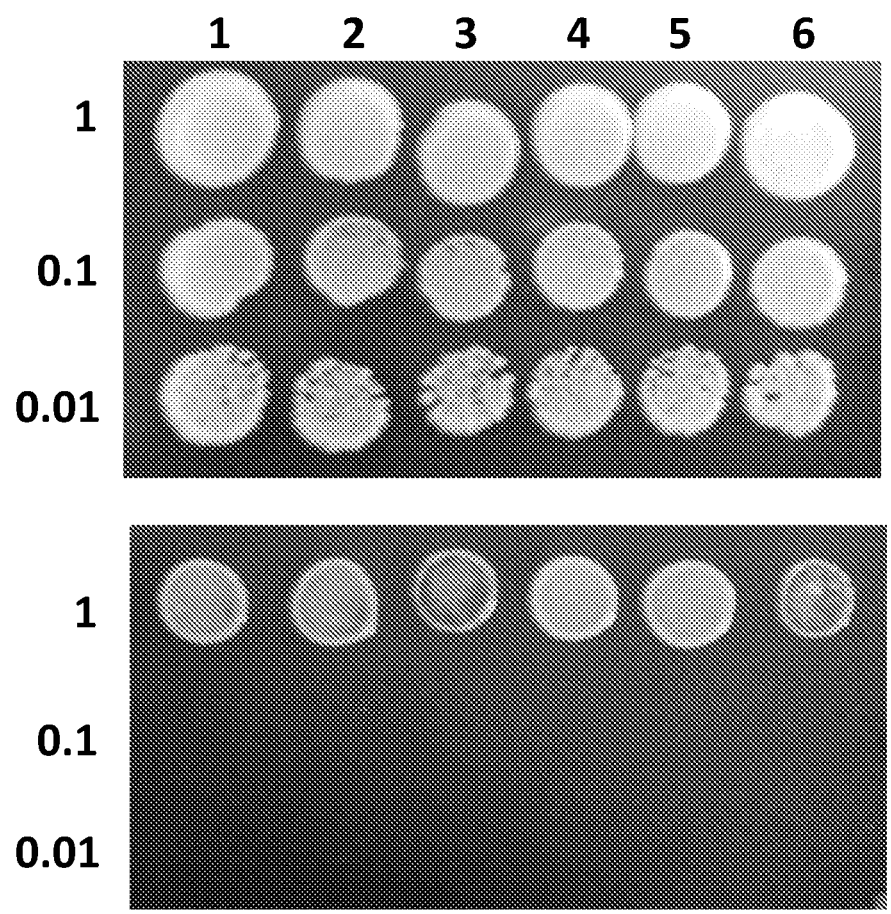
FIG. 16 depicts a solid media density assay showing increased ethanol tolerance in at least two S. cerevisiae strains (4 and 5) expressing the HpETT1 gene from H. polymorpha. Strain 1 is the control strain carrying only the S. cerevisiae plasmid vector Yep352, and strains 2-6 were separate isolates of transformants with that vector but carrying the H. polymorpha HpETT1 gene under control of a S. cerevisiae promoter. The upper panel is the control growth media (YNB plus sucrose, leu, lys and his) the lower panel is the same further containing 6% ethanol.
Figure 17:
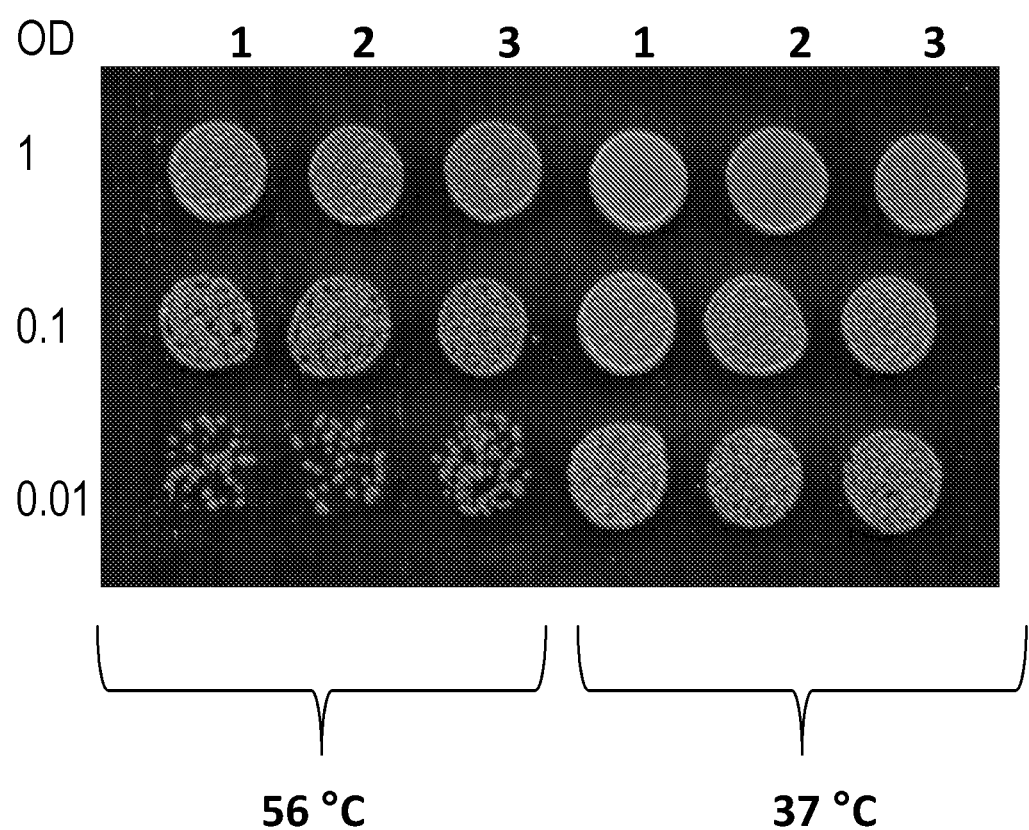
FIG. 17 depicts a solid media density assay showing increased heat shock tolerance of the 3Leu+pETT1-10 strain of H. polymorpha overexpressing the HpETT1 gene (3) in comparison to the parental control 3leu+ (2) and the strain MPE1Sc, which is 3Leu+ transformed with a vector to overexpress the S. cerevisiae MPE1 protein, when grown at 37° C. or heat shocked at 56° C. for 15 min prior to plating.
Figure 18:
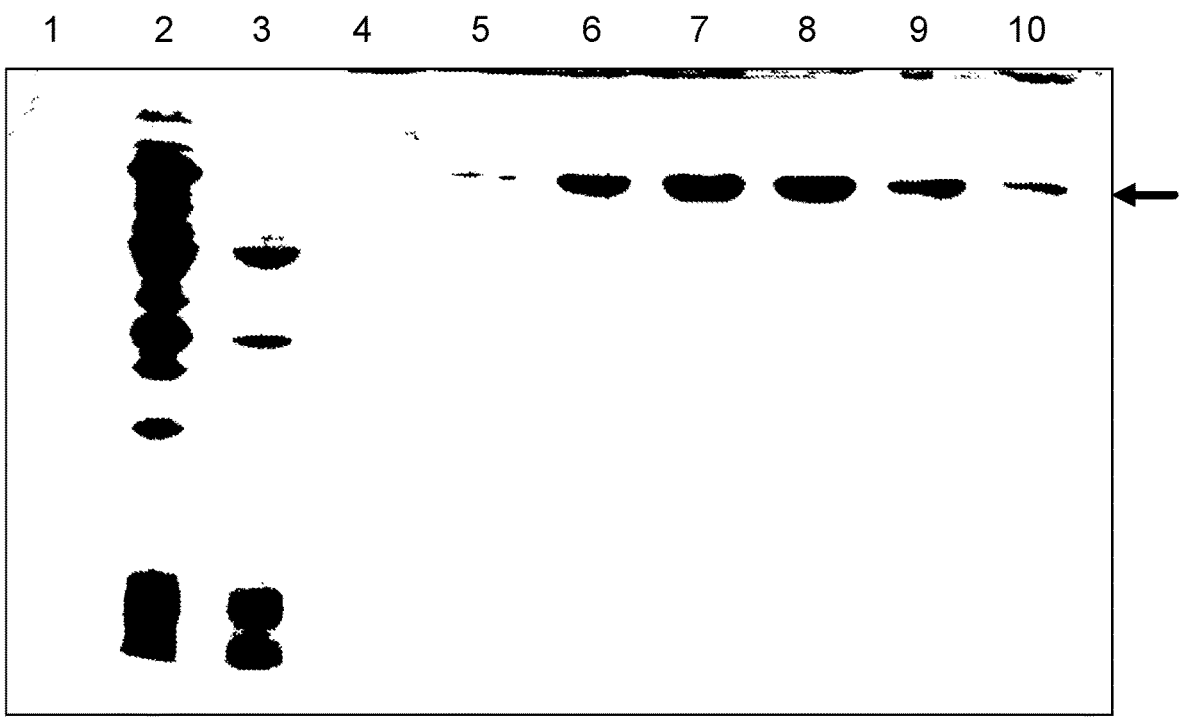
FIG. 18 shows a 12% SDS PAGE result demonstrating isolation of the HpEtt1 protein (arrow) after overexpression in E. coli using a his-tagged expression vector. Lane assignments: 1, protein ladder; 2, total soluble proteins before column; 3 soluble protein flow through; 4-9 fractions subsequently eluted from column.

The *H. polymorpha* HpEtt1 protein was overexpressed in bacteria as his tagged fusion protein, then isolated and partially purified as shown in the SDS polyacrylamide gel depicted in FIG. 14.

Discussion.

The *S. cerevisiae* Mpe1 protein was previously characterized as an essential evolutionary conserved protein participating in cleavage and polyadenylation of mRNA (Vo et al., 2001). The present disclosure demonstrates that an orthologue present in *H. polymorpha* that shares 39% sequence identity with the *S. cerevisiae* Mpe1 protein, which is herein designated HpEtt1 is involved in ethanol resistance and high temperature resistance in *H. polymorpha* and also confers a detectable increase in ethanol resistance when expressed in *S. cerevisiae*. Unlike its *S. cerevisiae* orthologue, the HpETT1 gene is not necessary for cell viability. The ability to functionally complement the *H. polymorpha* 7E mutant was used as a method to isolate another Ett1 like protein PsEtt1 from another xylose fermenting yeast. *P. stipitis*. The PsEtt1 protein shares about 37% amino acid Identity with the HpEtt1. Despite having similar sequence identity at 39% to the *S. cerevisiae* homologue MPE1, expression of the *S. cerevisiae* protein in the *H. polymorpha* 7E mutant, which lacks a functional HpETT1 gene did not restore the growth on 7% ethanol. In spite of being evolutionary conserved, Ett1 p of *H. polymorpha* as well as other xylose fermenting yeast species *P. stipitis* participate in ethanol resistance. It is noted that the sequence of the *H. polymorpha* HpETT1 contains several motifs (FIG. 4) recognized in the *S. cerevisiae* gene to be involved in mRNA maturation (i.e., an RNA-binding zinc knuckle domain) (Vo et al., 2001). The question about involving the *H. polymorpha* HpETT1 gene in mRNA maturation remains unclarified pending experimental evaluation.

The results described herein show that *H. polymorpha* ethanol tolerance could be substantially improved by introducing multiple copies of native ETT1 gene into the genome. The strain constructed in the present disclosure is a recombinant strain carrying 6-7 copies of ETT1 gene and has 10-fold higher resistance towards exogenous ethanol and improved growth kinetics in the ethanol media. Moreover, the corresponding multicopy integrant (3Leu+pETT1-10) proved to be more resistant to the protein misfolding reagent, AZC. The 7E mutant is unable to grow at 50 ° C., which is upper temperature limit to *H. polymorpha* (Guerra et al., 2005). Ethanol and temperature stresses cause some similar effects, particularly block of mature mRNA export from the nucleus and subsequently the accumulation of bulk poly $(A)^+$ mRNA in this cell compartment (Tani et al., 1995; Saavedra et al., 1996; Krebber et al., 1999). The defects in processes of mRNA maturation also cause the accumulation of bulk poly $(A)^+$ mRNA in the nucleus (Brodsky and Silver, 2000; Jensen et al., 2001). So it may be supposed that *H. polymorpha* Ett1Hp being a RNA-binding protein could influence the mRNA maturation under ethanol stress and high temperature but not under optimal growth conditions.

Strain NRRL Y-50838, was deposited under the terms of the Budapest Treaty on Apr. 3, 2013. The deposit was made to, and accepted by, the United Stated Department of Agriculture Research Service—National Center for Agriculture Utilization Research (USDA-ARS-NCAUR), 1815 North University Street, Peoria, Ill. 61604-3999.

REFERENCES

Brachmann, C. B., A. Davies, G. J. Cost, E. Caputo, J. Li, P. Hieter, and J. D. Boeke. 1998. Designer strains derived from *Saccharomyces cerevisiae* S288C: useful set of strains and plasmids for PCR-mediated gene disruption and other applications.Yeast 14: 115-132.

Brodsky, A. S. and Silver, P. A. (2000). Pre-mRNA processing factors are required for nuclear xport. RNA 6: 1737-1749.

Faber, K. N., P. Haima, W. Harder, M. Veenhuis, and G. Ab. 1994. Highly-efficient electrotransformation of the yeast *Hansenula polymorpha*. Curr Genet 25(4): 305-310.

Gellissen, G. 2000. Heterologous protein production in methylotrophic yeasts. Appl. Microbiol. Biotechnol. 54: 741-750.

Gellissen, G. (ed.). 2002. *Hansenula polymorpha*—Biology and Applications. Wiley-VCH, Weinheim.

Gleeson, M. A. G. and P. E. Sudbery. 1988. Genetic analysis in the methylotrophic yeast *Hansenula polymorpha*. Yeast 4: 293-303.

Guerra, E., P. P. Chye, E. Berardi and P. W. Piper. 2005. Hypoxia abolishes transience of the heat-shock response in the methylotrophic yeast *Hansenula polymorpha*. Microbiology 151: 805-811.

Ishchuk, O. P., A. Y. Voronovsky, O. V. Stasyk, G. Z. Gayda, M. V. Gonchar, C. A. Abbas, and A. A. Sibirny. 2008. Overexpression of pyruvate decarboxylase in the yeast *Hansenula polymorpha* results in increased ethanol yield in high-temperature fermentation of xylose. FEMS Yeast Res 7: 1167-1174.

Jensen, T. H., K. Patricio, T. McCarthy and M. Rosbash. 2001. A block to mRNA nuclear export in *S. cerevisiae* leads to hyperadenylation of transcripts that accumulate at the site of transcription. Mol Cell 7: 887-898.

Krebber, H., T. Taura, M. S. Lee and P. A. Silver. 1999. Uncoupling of hnRNP Npl3p from mRNAs during the stress-induced block in mRNA export. Genes Dev 13: 1994-2004.

Lahtchev, K. L., V. D. Semenova, I. I. Tolstorukov, I. van der Klei, and M. Veenhuis. 2002. Isolation and properties of genetically defined strains of the methylotrophic yeast *Hansenula polymorpha* CBS4732. Arch. Microbiol. 177: 150-158.

Lane, J. M., P. Dehm, and D. J. Prockop. 1971. Effect of the proline analogue azetidine-2-carboxylic acid on collagen synthesis in vivo. I. Arrest of collagen accumulation in growing chick embryos. Biochim Biophys Acta 236(3): 517-527.

Ryabova, O. B., O. M. Chmil, and A. A. Sibirny. 2003. Xylose and cellobiose fermentation to ethanol by the thermotelerant methylotrophic yeast *Hansenula polymorpha*. FEMS Yeast Res. 4(2): 157-164.

Saavedra, C., K. S. Tung, D.C. Amberg, A. K. Hopper, and C. N. Cole. 1996. Regulation of mRNA export in response to stress in *Saccharomyces cerevisiae*. Genes Dev 10: 1608-1620.

Sambrook, J., E. F. Fritsh, and T. Maniatis. 1989. Molecular Cloning: A Laboratory Manual, 2nd edition., Cold Spring Harbor, N.Y. : Cold Spring Harbor Laboratory.

Siverio, J. M. 2002. Biochemistry and genetics of nitrate assimilation. In . Gellissen (ed.), *Hansenula polymorpha*—Biology and Applications. Wiley-VCH, Weinheim.

Sohn, J. H., E. S. Choi, H. A. Kang, J. S. Rhee, M. O. Agaphonov, M. D. Ter-Avanesyan, and S. K. Rhee. 1999. A dominant selection system designed for copynumber—controlled gene integration in *Hansenula polymorpha* DL-1. Appl. Microbiol. Biotechnol. 51: 800-807.

Suckow, M., and G. Gellissen. 2002. The expression platform based on *H. polymorpha* strain RB11 and its derivatives—history,status and perspectives. In G. Gellissen (ed.), *Hansenula polymorpha*—Biology and Applications. Wiley-VCH, Weinheim.

Tani, T., R. J. Derby, Y. Hiraoka, and D. L. Spector. 1995. Nuclear accumulation of poly (A)+ RNA in heat-shocked yeast cells: implication of nucleolar involvement in mRNA transport. Mol. Biol. Cell 6: 1515-1534.

Trotter, E. W., C. M. Kao, L. Berenfeld, D. Botstein, G. A. Petsko, and J. V. Gray. 2002. Misfolded proteins are competent to mediate a subset of the responses to heat shock in *Saccharomyces cerevisiae*. J Biol Chem 277(47): 44817-44825.

Ubiyvovk, V. M., O. V. Blazhenko, D. Gigot, M. Penninckx, and A. A. Sibirny. 2006. Role of gamma-glutamyltranspeptidase in detoxification of xenobiotics in the yeasts *Hansenula polymorpha* and *Saccharomyces cerevisiae*. Cell Biol Int 30: 665-671.

Van der Klei, I. J., and M. Veenhuis. 2002. *Hansenula polymorpha:* a versatile model organism in peroxisome research. In G. Gellissen (ed.), *Hansenula polymorpha*—Biology and Applications. Wiley-VCH, Weinheim.

Vo, L. T., M. Minet, J. M. Schmitter, F. Lacroute, and F. Wyers. 2001. Mpe1, a zinc knuckle protein, is an essential component of yeast cleavage and polyadenylation factor required for the cleavage and polyadenylation of mRNA. Mol. Cell Biol. 21(24): 8346-8356.

Voronovsky, A., C. A. Abbas, L. R. Fayura, B. V. Kshanovska, K. V. Dmytruk, K. A. Sybirna and A. A. Sibirny. 2002. Development of a transformation system for the flavinogenic yeast *Candida famata*. FEMS Yeast Res. 2: 381-388.

Yang, V. W., J. A. Marks, B. Davis, and T. Jeffries. 1994. High-efficiency transformation of *Pichia stipitis* based on its URA3 gene and a homologous autonomous replication sequence, ARS2. Appl. Environ. Microbiol. 60: 4245-4254.

Zagari, A., G. N émethy, and H. A. Scheraga. 1990. The effect of the L-azetidine-2-carboxylic acid residue on protein conformation. I. Conformations of the residue and of dipeptides. Biopolymers 30(9-10): 951-959.

The invention claimed is:

1. A yeast transformed with an isolated nucleic acid comprising a promoter operably configured to overexpress a nucleic acid encoding at least one of a *H. polymorpha* ett1 protein according to SEQ. ID NO: 2 and a *P. stipitis* ett1 protein according to SEQ. ID NO: 4, wherein said transformed yeast exhibits greater tolerance to ethanol than a parent yeast that is otherwise identical but not transformed with said isolated nucleic acid.

2. The yeast of claim 1 wherein the yeast is selected from the group consisting of *H. polymorpha* and *S. cerevisiae*.

3. The yeast of claim 1 wherein said isolated nucleic acid is integrated in multiple copies into the genome of the yeast.

4. A method of making ethanol comprising growing the yeast of claim 1 in a medium under conditions selected to produce ethanol.

5. A strain of *H. polymorpha* that has a mutation in the ETT1 gene encoding a protein according to SEQ. ID NO: 2 wherein said mutation results in sensitivity to growth on medium containing ethanol in comparison to a parent strain of *H. polymorpha* that lacks such a mutation.

6. The strain of claim 5 designated 7E on deposit as NRRL Y-50838.

* * * * *